(12) United States Patent
Addison et al.

(10) Patent No.: US 9,011,347 B2
(45) Date of Patent: Apr. 21, 2015

(54) METHODS AND APPARATUS FOR DETERMINING BREATHING EFFORT CHARACTERISTICS MEASURES

(75) Inventors: Paul Stanley Addison, Edinburgh (GB); Andrew M. Cassidy, Edinburgh (GB); James N. Watson, Dunfermline (GB)

(73) Assignee: Nellcor Puritan Bennett Ireland, Galway (IE)

( * ) Notice: Subject to any disclaimer, the term of this patent is extended or adjusted under 35 U.S.C. 154(b) by 744 days.

(21) Appl. No.: 12/497,291

(22) Filed: Jul. 2, 2009

(65) Prior Publication Data

US 2011/0004081 A1 Jan. 6, 2011

(51) Int. Cl.
*A61B 5/02* (2006.01)
*A61B 5/08* (2006.01)
(Continued)

(52) U.S. Cl.
CPC ............... *A61B 5/08* (2013.01); *A61B 5/1455* (2013.01); *A61B 5/087* (2013.01); *A61B 5/726* (2013.01)

(58) Field of Classification Search
CPC ........ A61B 7/003; A61B 7/097; A61B 7/083; A61B 7/0836; A61B 7/085; A61B 7/1135; A61B 7/113; A61B 7/0809; A61B 7/0878; A61B 7/087; A61B 7/09; A61B 7/0871; A61B 7/093; A61B 7/095; A61M 16/00; A61N 1/3627
USPC ............... 600/486–488, 529–543; 128/204.1, 128/204.21–204.23, 204.26
See application file for complete search history.

(56) References Cited

U.S. PATENT DOCUMENTS 3,532,087 A 10/1970 Horn
3,884,219 A 5/1975 Richardson et al.
(Continued)

FOREIGN PATENT DOCUMENTS

JP 09-084776 3/1997
WO WO 00/021438 4/2000
(Continued)

OTHER PUBLICATIONS

"Respiratory Effort During Obstructive Sleep Apnea, Role of Age and Sleep State" by Krieger et al., Chest, vol. 112, Iss. 4, Oct. 1997.*
(Continued)

*Primary Examiner* — Patricia Mallari
*Assistant Examiner* — Vasuda Ramachandran
(74) *Attorney, Agent, or Firm* — Shvarts & Leiz LLP

(57) ABSTRACT

One or more respiratory characteristics of a patient are measured by coupling patient monitor apparatus (e.g., a photoplethysmograph ("PPG")) to the patient in order to produce a patient monitor signal that includes signal indicia indicative of effort the patient is exerting to breathe. A breathing or respiratory effort signal for the patient is extracted from the patient monitor signal. A respiratory characteristic signal is extracted (at least in part) from the effort signal. This may be done, for example, on the basis of an amplitude feature of the effort signal and a relative time of occurrence of that amplitude feature. Alternatively, the respiratory characteristic signal may be based on a relationship between two amplitude features of the effort signal, with or without regard for specifics of the times of occurrence of those amplitude features. A breath air flow meter may also be coupled to the patient, if desired, in order to produce a flow signal. One or more of the respiratory characteristic measures may also be partly based on the flow signal.

17 Claims, 27 Drawing Sheets
(1 of 27 Drawing Sheet(s) Filed in Color)

(51) Int. Cl.

| | |
|---|---|
| A61B 5/00 | (2006.01) |
| A61B 5/1455 | (2006.01) |
| A61B 5/087 | (2006.01) |

(56) References Cited

U.S. PATENT DOCUMENTS

| | | | |
|---|---|---|---|
| 3,926,177 | A | 12/1975 | Hardway et al. |
| 4,289,141 | A | 9/1981 | Cormier |
| 4,696,307 | A | 9/1987 | Montgieux |
| 5,143,078 | A | 9/1992 | Mather |
| 5,273,036 | A | 12/1993 | Kronberg |
| 5,439,483 | A | 8/1995 | Duong-Van |
| 5,485,851 | A | 1/1996 | Erickson |
| 5,575,284 | A | 11/1996 | Athan |
| 5,590,650 | A | 1/1997 | Genova |
| 5,632,272 | A | 5/1997 | Diab et al. |
| 5,680,871 | A | 10/1997 | Ganshorn |
| 5,682,898 | A | 11/1997 | Aung |
| 5,778,881 | A | 7/1998 | Sun et al. |
| 5,795,304 | A | 8/1998 | Sun et al. |
| 5,797,840 | A | 8/1998 | Akselrod |
| 5,827,195 | A | 10/1998 | Lander |
| 5,967,995 | A | 10/1999 | Shusterman et al. |
| 6,002,952 | A | 12/1999 | Diab et al. |
| 6,036,653 | A | 3/2000 | Baba et al. |
| 6,094,592 | A | 7/2000 | Yorkey |
| 6,095,984 | A | 8/2000 | Amano et al. |
| 6,117,075 | A | 9/2000 | Barnea |
| 6,129,675 | A | 10/2000 | Jay |
| 6,135,966 | A | 10/2000 | Ko |
| 6,142,953 | A | 11/2000 | Burton |
| 6,171,257 | B1 | 1/2001 | Weil et al. |
| 6,171,258 | B1 | 1/2001 | Karakasoglu et al. |
| 6,208,951 | B1 | 3/2001 | Kumar et al. |
| 6,293,915 | B1 | 9/2001 | Amano et al. |
| 6,325,761 | B1 | 12/2001 | Jay |
| 6,361,501 | B1 | 3/2002 | Amano et al. |
| 6,363,270 | B1 | 3/2002 | Colla et al. |
| 6,393,311 | B1 | 5/2002 | Edgar, Jr. et al. |
| 6,398,727 | B1 | 6/2002 | Bui et al. |
| 6,561,986 | B2 | 5/2003 | Baura |
| 6,608,934 | B2 | 8/2003 | Scheirer |
| 6,654,623 | B1 | 11/2003 | Kastle |
| 6,702,752 | B2 | 3/2004 | Dekker |
| 6,709,402 | B2 | 3/2004 | Dekker |
| 6,748,252 | B2 | 6/2004 | Lynn et al. |
| 6,758,216 | B1 * | 7/2004 | Berthon-Jones et al. 128/204.23 |
| 6,801,798 | B2 | 10/2004 | Geddes et al. |
| 6,810,277 | B2 | 10/2004 | Edgar, Jr. et al. |
| 6,811,538 | B2 | 11/2004 | Westbrook et al. |
| 6,896,661 | B2 | 5/2005 | Dekker |
| 6,909,912 | B2 | 6/2005 | Melker |
| 6,918,878 | B2 | 7/2005 | Brodnick |
| 6,930,608 | B2 | 8/2005 | Grajales et al. |
| 6,931,269 | B2 | 8/2005 | Terry |
| 6,990,426 | B2 | 1/2006 | Yoon et al. |
| 7,001,337 | B2 | 2/2006 | Dekker |
| 7,020,507 | B2 | 3/2006 | Scharf et al. |
| 7,024,235 | B2 | 4/2006 | Melker et al. |
| 7,025,730 | B2 | 4/2006 | Cho et al. |
| 7,035,679 | B2 | 4/2006 | Addison |
| 7,043,293 | B1 | 5/2006 | Baura |
| 7,052,469 | B2 | 5/2006 | Minamiura et al. |
| 7,054,453 | B2 | 5/2006 | Causevic |
| 7,054,454 | B2 | 5/2006 | Causevic et al. |
| 7,079,888 | B2 | 7/2006 | Oung |
| 7,127,278 | B2 | 10/2006 | Melker et al. |
| 7,171,251 | B2 | 1/2007 | Sarussi |
| 7,171,269 | B1 | 1/2007 | Addison |
| 7,173,525 | B2 | 2/2007 | Albert |
| 7,203,267 | B2 | 4/2007 | De Man et al. |
| 7,225,013 | B2 | 5/2007 | Geva et al. |
| 7,246,618 | B2 | 7/2007 | Habashi |
| 7,254,500 | B2 | 8/2007 | Makeig |
| 7,289,835 | B2 | 10/2007 | Mansfield |
| 7,344,497 | B2 | 3/2008 | Kline |
| 7,381,185 | B2 | 6/2008 | Zhirnov et al. |
| 7,398,115 | B2 | 7/2008 | Lynn |
| 7,421,296 | B1 | 9/2008 | Benser et al. |
| 7,515,949 | B2 | 4/2009 | Norris |
| 7,519,488 | B2 | 4/2009 | Fu |
| 7,523,011 | B2 | 4/2009 | Akiyama et al. |
| 2003/0163057 | A1 | 8/2003 | Flick et al. |
| 2005/0022606 | A1 | 2/2005 | Partin et al. |
| 2005/0043616 | A1 | 2/2005 | Chinchoy |
| 2005/0109340 | A1 | 5/2005 | Tehrani |
| 2005/0122222 | A1 | 6/2005 | Takasuka |
| 2005/0215915 | A1 | 9/2005 | Noda et al. |
| 2005/0222502 | A1 | 10/2005 | Cooper |
| 2005/0251056 | A1 | 11/2005 | Gribkov et al. |
| 2006/0074333 | A1 | 4/2006 | Huiku |
| 2006/0155206 | A1 | 7/2006 | Lynn |
| 2006/0209631 | A1 | 9/2006 | Melese et al. |
| 2006/0211930 | A1 | 9/2006 | Scharf et al. |
| 2006/0217603 | A1 | 9/2006 | Nagai et al. |
| 2006/0229519 | A1 | 10/2006 | Fujiwara et al. |
| 2006/0241506 | A1 | 10/2006 | Melker et al. |
| 2006/0258921 | A1 * | 11/2006 | Addison et al. ............... 600/323 |
| 2006/0265022 | A1 | 11/2006 | John et al. |
| 2006/0282001 | A1 | 12/2006 | Noel et al. |
| 2007/0000494 | A1 * | 1/2007 | Banner et al. ............ 128/204.23 |
| 2007/0016093 | A1 * | 1/2007 | Rapoport et al. ........ 128/204.23 |
| 2007/0021673 | A1 | 1/2007 | Arbel et al. |
| 2007/0027375 | A1 | 2/2007 | Melker et al. |
| 2007/0062531 | A1 | 3/2007 | Fisher et al. |
| 2007/0073120 | A1 | 3/2007 | Li et al. |
| 2007/0073124 | A1 | 3/2007 | Li et al. |
| 2007/0129647 | A1 | 6/2007 | Lynn |
| 2007/0149883 | A1 | 6/2007 | Yesha |
| 2007/0167694 | A1 | 7/2007 | Causevic et al. |
| 2007/0167851 | A1 | 7/2007 | Vitali et al. |
| 2007/0282212 | A1 | 12/2007 | Sierra et al. |
| 2008/0045832 | A1 | 2/2008 | McGrath |
| 2008/0060138 | A1 | 3/2008 | Price et al. |
| 2008/0066753 | A1 | 3/2008 | Martin |
| 2008/0076992 | A1 | 3/2008 | Hete et al. |
| 2008/0082018 | A1 | 4/2008 | Sackner et al. |
| 2008/0092898 | A1 | 4/2008 | Schneider et al. |
| 2008/0119756 | A1 | 5/2008 | Wada |
| 2008/0171946 | A1 | 7/2008 | Hansmann |
| 2008/0190430 | A1 | 8/2008 | Melker et al. |
| 2008/0202525 | A1 | 8/2008 | Mitton et al. |
| 2008/0214903 | A1 | 9/2008 | Orbach |
| 2008/0243021 | A1 | 10/2008 | Causevic et al. |

FOREIGN PATENT DOCUMENTS

| | | |
|---|---|---|
| WO | WO 01/025802 | 4/2001 |
| WO | WO 01/062152 | 8/2001 |
| WO | WO 01/076471 | 10/2001 |
| WO | WO 03/000125 | 1/2003 |
| WO | WO 03/055395 | 7/2003 |
| WO | WO 2004/075746 | 9/2004 |
| WO | WO 2004/105601 | 12/2004 |
| WO | WO 2005/096170 | 10/2005 |
| WO | WO 2006/085120 | 8/2006 |
| WO | WO 2008/043864 | 4/2008 |
| WO | 2010/001232 A1 | 1/2010 |

OTHER PUBLICATIONS

Addison, Paul S., The Illustrated Wavelet Transform Handbook, Taylor & Francis Group, 2002.

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International

(56) References Cited

OTHER PUBLICATIONS

Journal of Wavelets, Multiresolution and Information Processing, vol. 3, No. 1, 2005, pp. 1-24.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, vol. 20, No. 1, 2006, pp. 33-36.

Leonard, Paul A., Clifton, David, Addison, Paul S., Watson, James N., Beattie, Tom "An Automated Algorithm for Determining Respiratory Rate by Photoplethysmogram in Children," Acta Paediatrica, 2006; 95: 1124-1128.

Yamada, Michio, "Wavelet Analysis and Its Application," Journal of the Institute of Electronics, Information and Communication Engineers, vol. 76, No. 5, May 1993, pp. 518-528.

International Search Report PCT/IB32010/001675, 4 pages, mailed Oct. 6, 2010.

* cited by examiner

METHODS AND APPARATUS FOR DETERMINING BREATHING EFFORT CHARACTERISTICS MEASURES

CROSS REFERENCE TO RELATED APPLICATIONS

Portions of this specification will also be found in Addison et al. U.S. patent application Ser. No. 12/245,366, filed Oct. 3, 2008, which is hereby incorporated by reference herein in its entirety.

SUMMARY OF THE DISCLOSURE

The present disclosure relates to signal processing and, more particularly, the present disclosure relates to using continuous wavelet transforms for processing, for example, a photoplethysmograph (PPG) signal, to determine effort, such as respiratory effort of a patient.

Systems and methods to analyze the suitable signal domain representation in order to determine effort are disclosed herein. In one embodiment, effort may relate to a measure of strength of at least one repetitive feature in a signal. In another embodiment, effort may relate to physical effort of a process that may affect the signal (e.g., effort may relate to work of a process).

In some embodiments, the use of a transform may allow a signal to be represented in a suitable domain such as, for example, a scalogram (in a time-scale domain) or a spectrogram (in a time-frequency domain). A type of effort which may be determined by analyzing the signal representation may be, for example, breathing effort of a patient. The breathing effort of the patient may be determined by analyzing a scalogram with the processes presented in this disclosure.

The determination of effort from a scalogram or any other signal representation is possible because changes in effort induce or change various features of the signal used to generate the scalogram. For example, the act of breathing may cause a breathing band to become present in a scalogram that was derived from a PPG signal. This band may occur at or about the scale having a characteristic frequency that corresponds to the breathing frequency. Furthermore, the features within this band or other bands on the scalogram (e.g., energy, amplitude, phase, or modulation) may result from changes in breathing and/or breathing effort and therefore may be correlated with the patient's breathing effort.

The effort determined by the methods and systems described herein may be represented in any suitable way. For example, breathing effort may be represented graphically in which changes in features of the breathing band and of neighboring bands are represented by changes in color or pattern.

Alternatively, or in combination with the graphical representation, a quantitative value indicative of the relative change in effort or of an absolute value of effort may be calculated according to any suitable metric.

In addition, thresholds may be set to trigger alarms if effort increases (e.g., by percent change or absolute value) over the threshold.

In one embodiment, the present disclosure may be used in the context of a sleep study environment to detect and/or differentiate apneic events. In an embodiment, the present disclosure may be used to monitor the effect of therapeutic intervention.

In accordance with certain possible aspects of the disclosure, a patient is coupled to apparatus for monitoring the effort the patient is applying to breathing ("patient monitor apparatus" or "breathing effort monitoring apparatus").

Although other examples of effort monitoring apparatus will be mentioned later in this disclosure, an illustrative embodiment employs photoplethysmograph ("PPG") apparatus. Such a PPG embodiment will be referred to for the most part in this introductory portion of the disclosure.

The above-mentioned PPG apparatus produces a PPG signal for the patient. First circuitry is provided for extracting a patient breathing effort signal from the PPG signal. Second circuitry is provided for extracting from the effort signal a respiratory characteristic signal for the patient based on at least one amplitude feature of the effort signal and a relative time of occurrence of that amplitude feature. Examples of amplitude features that may be used are a minimum amplitude, a maximum amplitude, elapsed time from a minimum amplitude to a subsequent maximum amplitude, elapsed time from a maximum amplitude to a next subsequent maximum amplitude, ratio between two such elapsed time characteristics, ratio between a maximum amplitude and a minimum amplitude, ratio between an amplitude feature (or the difference between two amplitude features) and the elapsed time between two amplitude features (e.g., to give a measure of the slope or first derivative of the effort signal), etc.

In accordance with certain further possible aspects of the disclosure, the patient may also be coupled to respiratory air flow meter apparatus for producing a flow signal indicative of air flow to and from the patient's lungs as a result of breathing by the patient. The respiratory characteristic signal for the patient may then also be based in part on the flow signal (e.g., a flow signal amplitude feature and the relative time of occurrence of that flow signal amplitude feature). Examples of flow signal amplitude features that may be used are cessation of effective breathing by the patient, duration of a period of effective breathing by the patient, etc. Examples of breathing characteristic signals that are based on information from both the effort signal and the flow signal are elapsed time from cessation of effective breathing (from the flow signal) to the start of increasing effort by the patient to breath (from the effort signal), ratio of that breathing characteristic signal to either (1) elapsed time between maxima in the effort signal or (2) duration of period of effective breathing (from the flow signal), etc.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features of the present disclosure, its nature and various advantages will be more apparent upon consideration of the following detailed description, taken in conjunction with the accompanying drawings in which.

DETAILED DESCRIPTION

Figure 1:
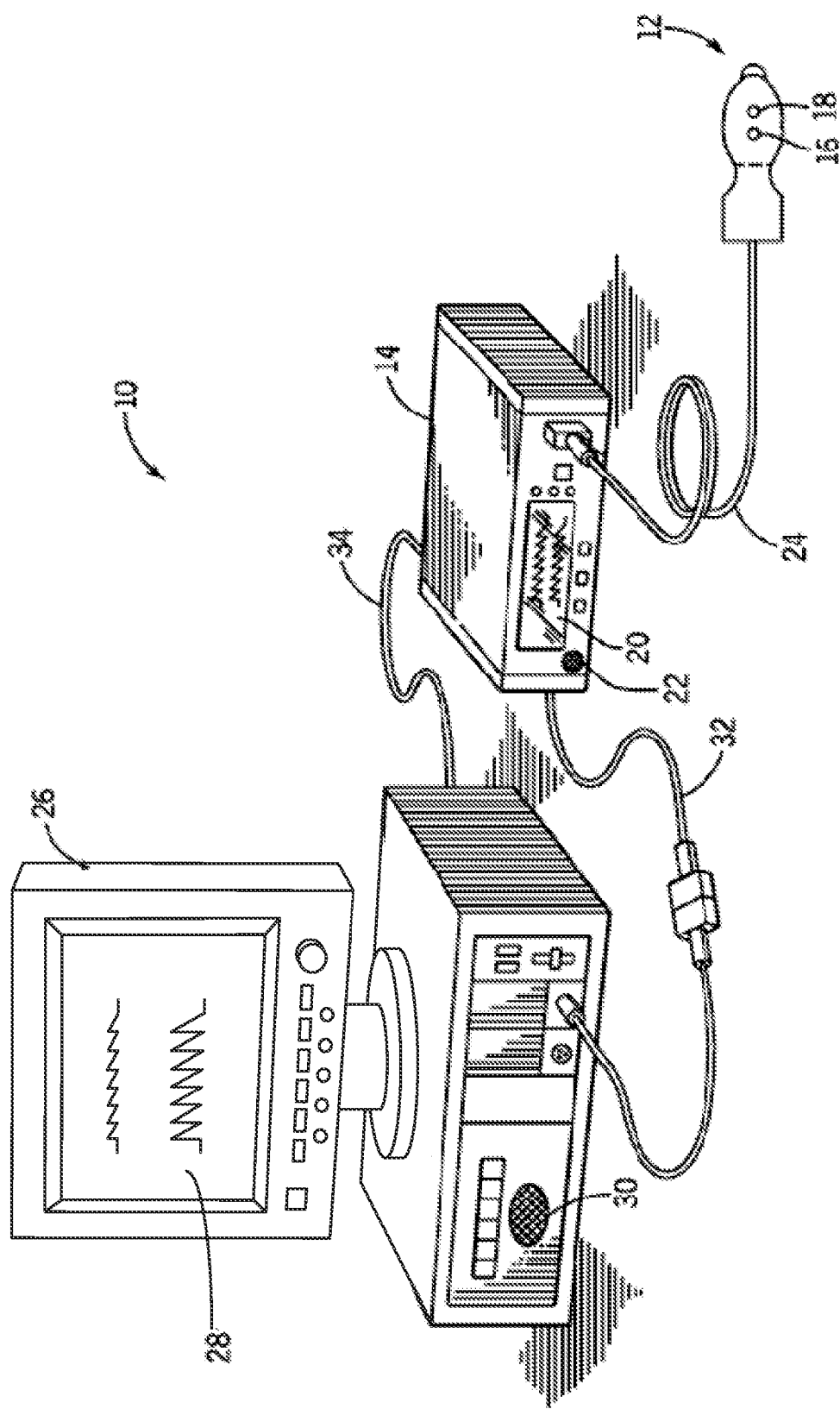
FIG. 1 shows an illustrative effort system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood. Pulse oximeters may also be used to determine respiratory effort in accordance with the present disclosure.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based at least in part on Lambert-Beer's law. The following notation will be used herein:

$$I(\lambda,t)=I_0(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R)+(1-s)\beta_r(\lambda_R)}{s\beta_o(\lambda_{IR})+(1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR})-\beta_r(\lambda_{IR})) - \frac{d\log I(\lambda_{IR})}{dt}(\beta_o(\lambda_R)-\beta_r(\lambda_R))}$$

Note in discrete time $$\frac{d \log I(\lambda, t)}{dt} \simeq \log I(\lambda, t_2) - \log I(\lambda, t_1)$$

Using log A - log B = log A/B, $$\frac{d \log I(\lambda, t)}{dt} \simeq \log\left(\frac{I(t_2, \lambda)}{I(t_1, \lambda)}\right)$$

So, (4) can be rewritten as $$\frac{\frac{d \log I(\lambda_R)}{dt}}{\frac{d \log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d \log I}{dt} = \frac{dI/dt}{I} \quad (6)$$

now (5) becomes $$\frac{\frac{d \log I(\lambda_R)}{dt}}{\frac{d \log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t) = [I(t_2, \lambda_{IR}) - I(t_1, \lambda_{IR})]I(t_1, \lambda_R)$$

$$y(t) = [I(t_2, \lambda_R) - I(t_1, \lambda_R)]I(t_1, \lambda_{IR})$$

$$y(t) = Rx(t) \quad (8)$$

FIG. 1 is a perspective view of an embodiment of an effort system 10. In an embodiment, effort system 10 is implemented as part of a pulse oximetry system. System 10 may include a sensor 12 and a monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

Sensor 12 or monitor 14 may further include, but are not limited to software modules that calculate respiration rate, airflow sensors (e.g., nasal thermistor), ventilators, chest straps, transthoracic sensors (e.g., sensors that measure transthoracic impedence).

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the effort or oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, effort system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's respiratory effort or blood oxygen saturation (referred to as an "$SpO_2$" measurement) generated by monitor 14, pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
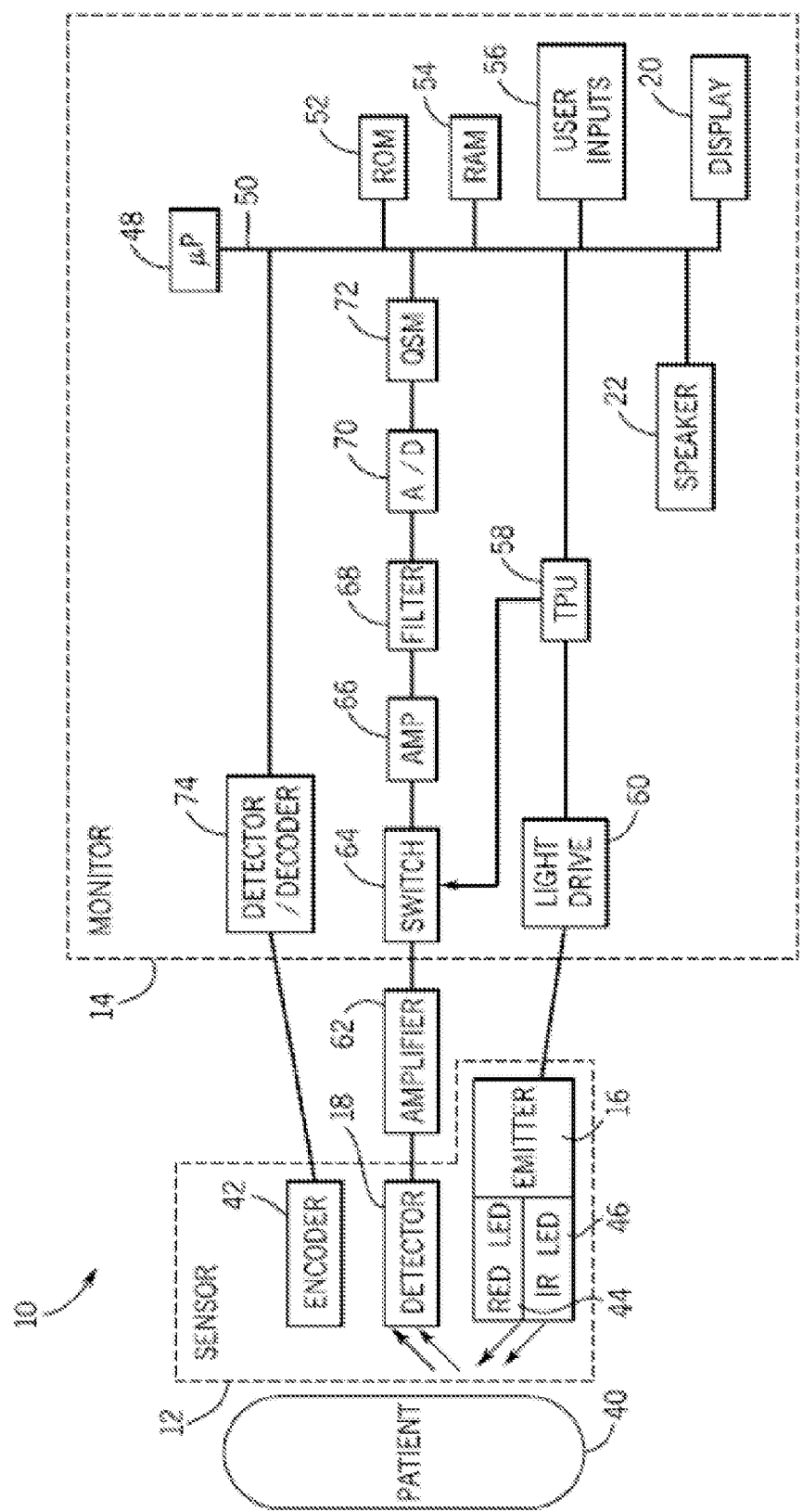
FIG. 2 is a block diagram of the illustrative effort system of FIG. 1 coupled to a patient in accordance with an embodiment.

FIG. 2 is a block diagram of an effort system, such as effort system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit one or more wavelengths of light (e.g., RED and/or IR) into a patient's tissue 40. Hence, emitter 16 may include a RED light emitting light source such as RED light emitting diode (LED) 44 and/or an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelength or wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as effort, $SpO_2$, and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing effort and pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a,b) = \frac{1}{\sqrt{a}} \int_{-\infty}^{+\infty} x(t) \psi^*\left(\frac{t-b}{a}\right) dt \quad (9)$$

where ψ*(t) is the complex conjugate of the wavelet function ψ(t), a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \tag{10}$$

where '| |' is the modulus operator. The scalogram may be rescaled for useful purposes. One common rescaling is defined as $$S_R(a,b) = \frac{|T(a,b)|^2}{a} \tag{11}$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \tag{12}$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t)=\pi^{-1/4}(e^{i2\pi f_0 t}-e^{-(2\pi f_0)^2/2})e^{-t^2/2} \tag{13}$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \tag{14}$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
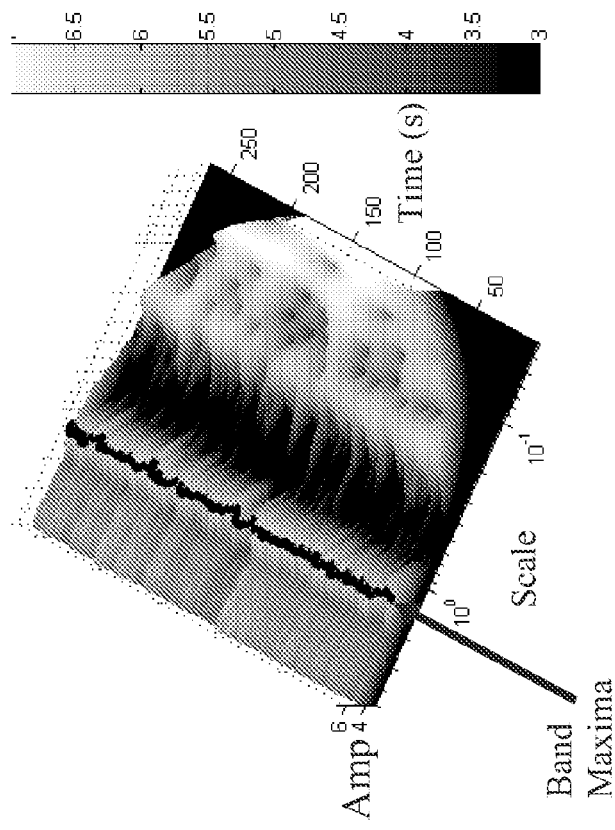
FIGS. 3(a) and 3(b) show illustrative views of a scalogram derived from a PPG signal in accordance with an embodiment.
Figure 3A:
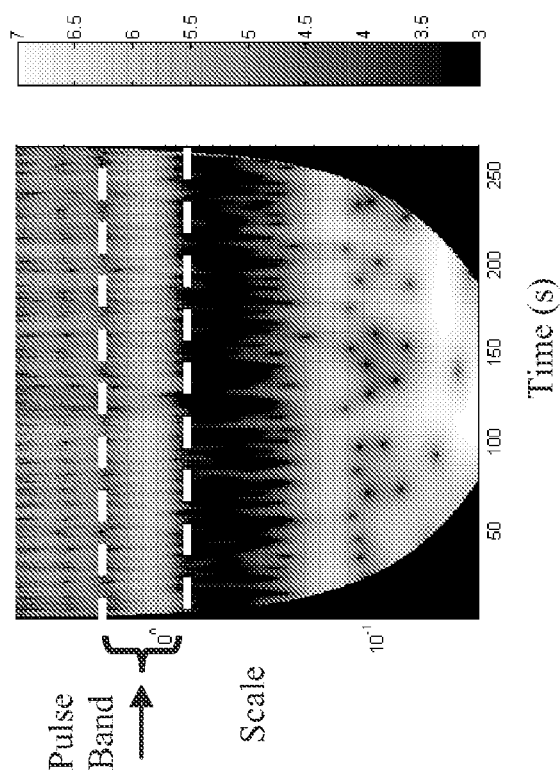

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
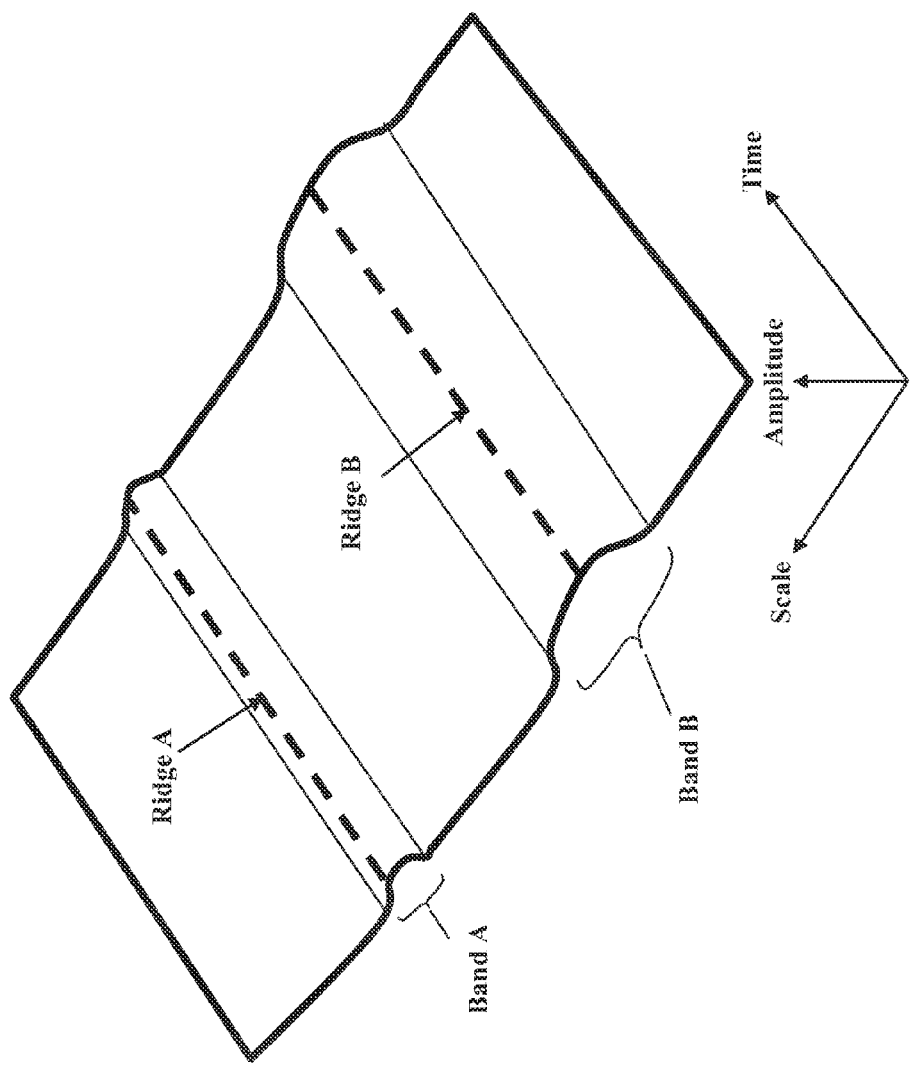
FIG. 3(c) shows an illustrative scalogram derived from a signal containing two pertinent components in accordance with an embodiment.
Figure 3D:
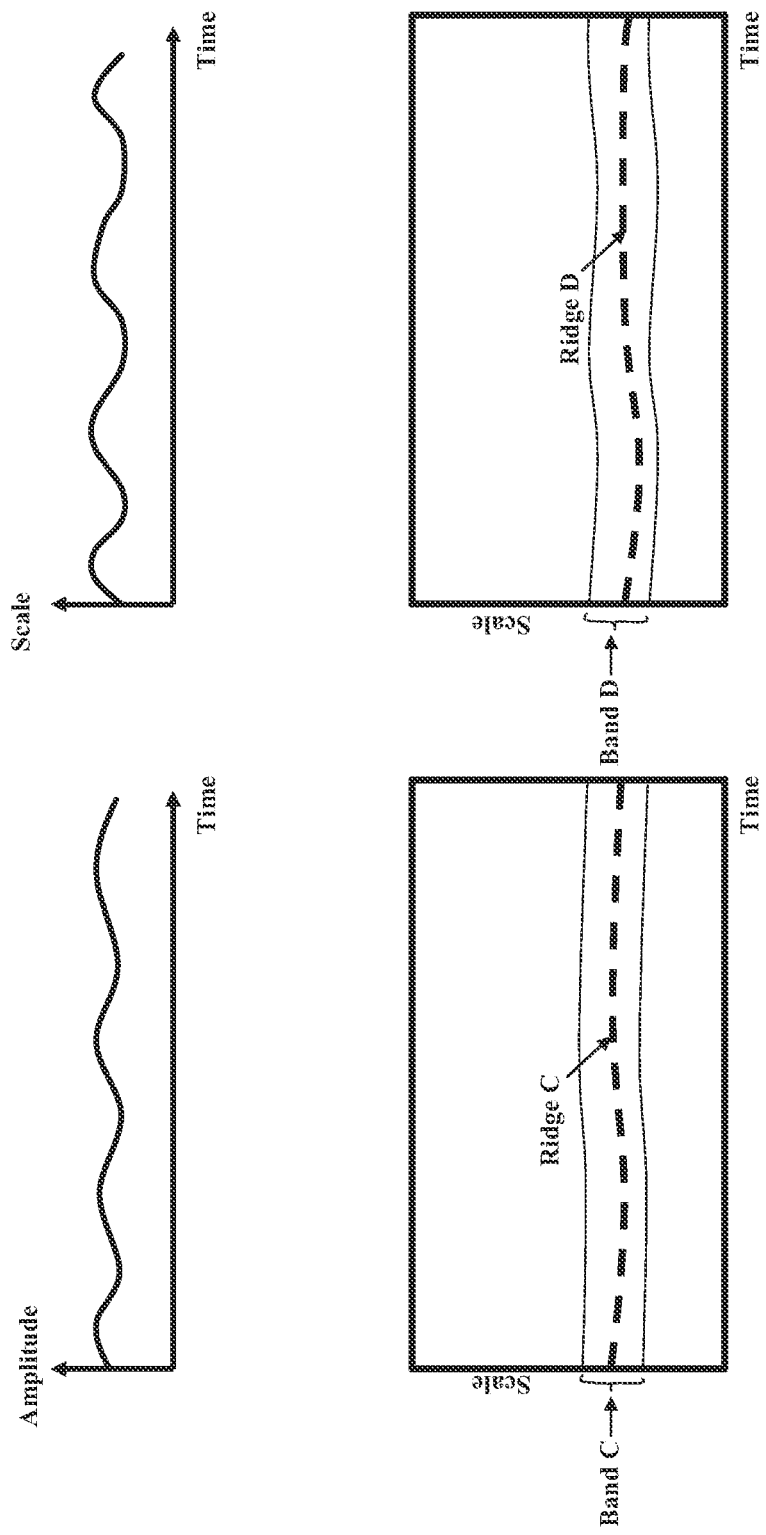
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In an embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_0^{\infty} T(a,b) \psi_{a,b}(t) \frac{da\,db}{a^2} \quad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (17)$$

Figure 3E:
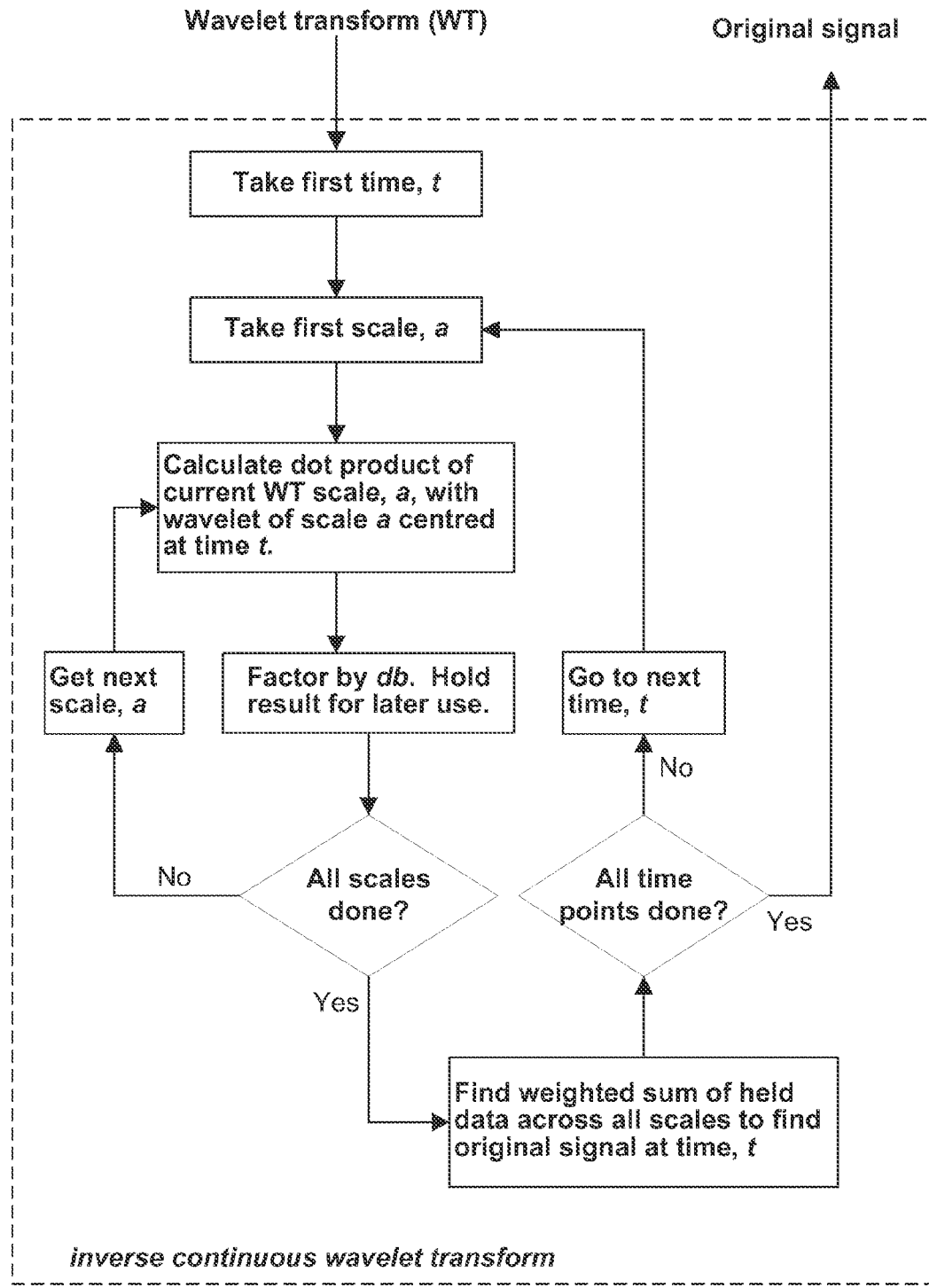
FIGS. 3(e) and 3(f) are flow charts of illustrative steps involved in performing an inverse continuous wavelet transform in accordance with embodiments.
Figure 3F:
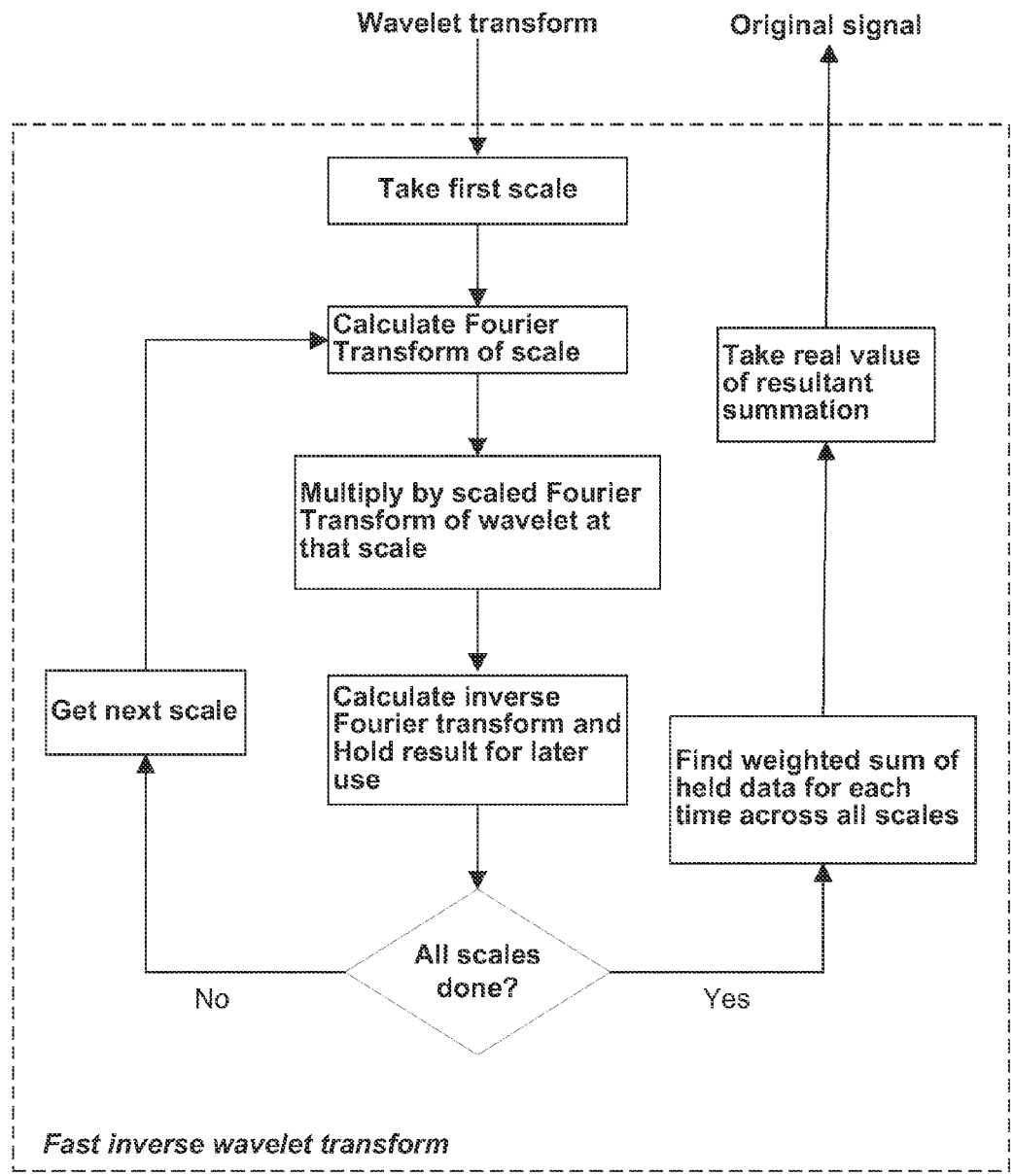

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

The present disclosure relates to methods and systems for processing a signal using the above mentioned techniques and analyzing the results of the techniques to determine effort. In one embodiment, effort may relate to a measure of strength of at least one repetitive feature in a signal. In another embodiment, effort may relate to physical effort of a process that may affect the signal (e.g. effort may relate to work of a process). For example, effort calculated from a PPG signal may relate to the respiratory effort of a patient. Respiratory effort may increase, for example, if a patient's respiratory pathway becomes restricted or blocked. Conversely, respiratory effort may decrease as a patient's respiratory pathway becomes unrestricted or unblocked. The effort of a signal may be determined, for example, by transforming the signal using a wavelet transform and analyzing features of a scalogram derived from the wavelet transform. In particular, changes in the features of the pulse band and breathing band in the scalogram may be correlated to a change in breathing effort.

As an additional example, the methods and systems disclosed herein may be used to determine effort in a mechanical engine. Over time, a mechanical engine may become less efficient because of wear of the mechanical parts and/or insufficient lubrication. This may cause extra strain on the engine parts and, in particular, cause the engine to exert more effort, work, or force to complete a process. Engine function may be monitored and represented using signals. These signals may be transformed and analyzed to determine effort using the techniques described herein. For example, an engine may oscillate in a particular manner. This oscillation may produce a band or bands within a scalogram. Features of this band or bands may change as the engine exerts more or less effort. The change in the features may then be correlated to effort.

It will be understood that the present disclosure is applicable to any suitable signals and that PPG signals or mechanical monitoring signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

The methods for determining effort described in this disclosure may be implemented on a multitude of different systems and apparatuses through the use of human-readable or machine-readable information. For example, the methods described herein maybe implemented using machine-readable computer code and executed on a computer system that is capable of reading the computer code. An exemplary system that is capable of determining effort is depicted in FIG. 4.

Figure 4:
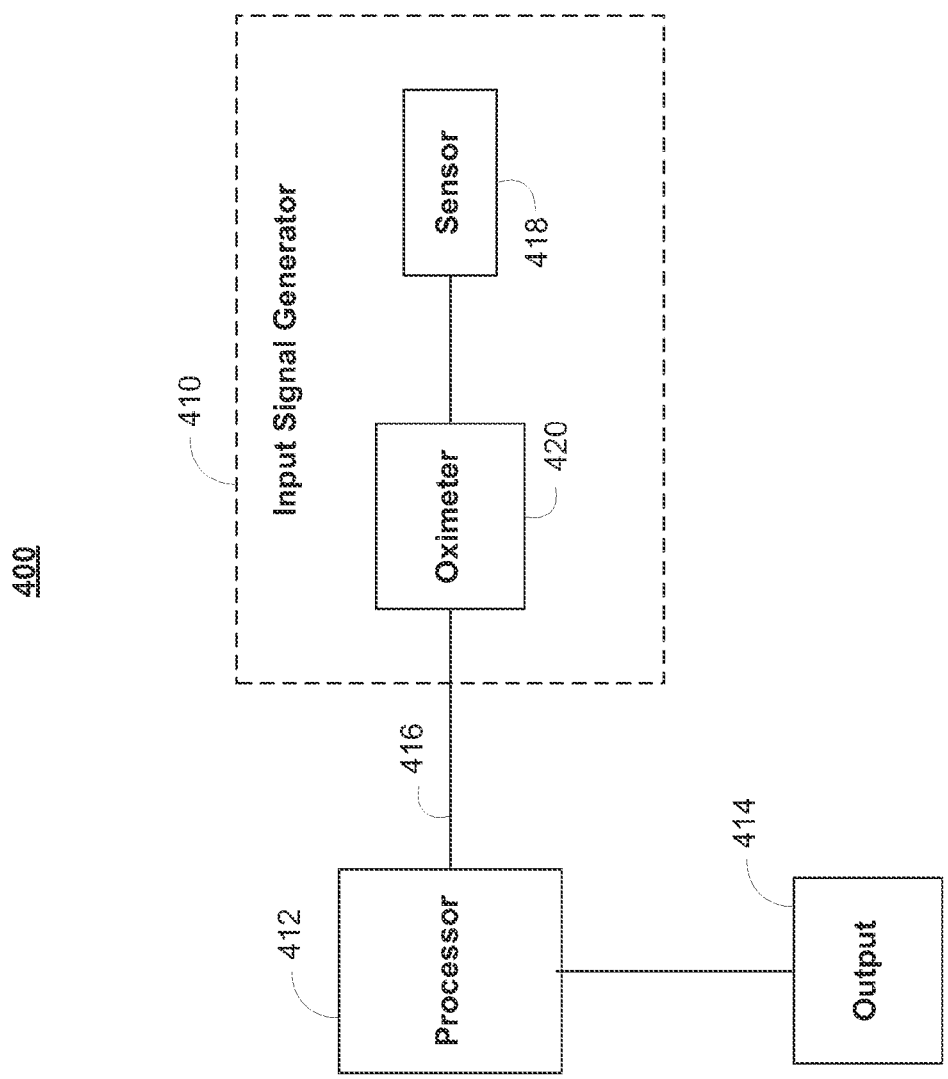
FIG. 4 is a block diagram of an illustrative continuous wavelet processing system in accordance with some embodiments.

FIG. 4 is an illustrative continuous wavelet processing system in accordance with an embodiment. In an embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In an embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

In some embodiments, in order to determine effort, processor 412 may first transform the signal into any suitable domain, for example, a Fourier, wavelet, spectral, scale, time, time-spectral, time-scale domains, or any transform space. Processor 412 may further transform the original and/or transformed signals into any of the suitable domains as necessary.

Processor 412 may represent the original or transformed signals in any suitable way, for example, through a two-dimensional representation or three-dimensional representation, such as a spectrogram or scalogram.

After processor 412 represents the signals in a suitable fashion, processor 412 may then find and analyze selected features in the signal representation of signal 416 to determine effort. Selected features may include the value, weighted value, or change in values with regard to energy, amplitude, frequency modulation, amplitude modulation, scale modulation, differences between features (e.g., distances between ridge amplitude peaks within a time-scale band).

For example, selected features may include features in a time-scale band in wavelet space or a rescaled wavelet space described above. As an illustrative example, the amplitude or energy of the band may be indicative of the breathing effort of a patient when the band is the patient's breathing band. Furthermore, changes in the amplitude or energy of the band may be indicative of a change in breathing effort of a patient. Other time-scale bands may also provide information indicative of breathing effort. For example, amplitude modulation, or scale modulation of a patient's pulse band may also be indicative of breathing effort. Effort may be correlated with any of the above selected features, other suitable features, or any combination thereof.

The selected features may be localized, repetitive, or continuous within one or more regions of the suitable domain space representation of signal 416. The selected features may not necessarily be localized in a band, but may potentially be present in any region within a signal representation. For example, the selected features may be localized, repetitive, or continuous in scale or time within a wavelet transform surface. A region of a particular size and shape may be used to analyze selected features in the domain space representation of signal 416. The region's size and shape may be selected based at least in part on the particular feature to be analyzed. As an illustrative example, in order to analyze a patient's breathing band for one or more selected features, the region may be selected to have an upper and lower scale value in the time-scale domain such that the region covers a portion of the band, the entire band, or the entire band plus additional portions of the time-scale domain. The region may also have a selected time window width.

The bounds of the region may be selected based at least in part on expected locations of the features. For example, the expected locations may be based at least in part on empirical data of a plurality of patients. The region may also be selected based at least in part on patient classification. For example, an adult's breathing band location generally differs from the location of a neonatal patient's breathing band. Thus, the region selected for an adult may be different than the region selected for a neonate.

In some embodiments, the region may be selected based at least in part on features within a scalogram. For example, the scalogram for a patient may be analyzed to determine the location of the breathing band and its corresponding ridge. The breathing band ridge may be located using standard ridge detection techniques. Ridges may also be detected using the techniques described in Watson et al., U.S. application Ser. No. 12/245,326, filed Oct. 3, 2008, entitled "Systems and Methods for Ridge Selection in Scalograms of Signals," which is incorporated by reference herein in its entirety. As an illustrative example, if the ridge of a band were found to be at location X, the region may be selected to extend a predetermined distance above and below location X. Alternatively, the band itself may be analyzed to determine its size. The upper and lower bounds of the band may be determined using one or more predetermined or adaptive threshold values. For example, the upper and lower bounds of the band may be determined to be the location where the band crosses below a threshold. The width of the region may be a predetermined amount of time or it may vary based at least in part on the characteristics of the original signal or the scalogram. For example, if noise is detected, the width of the region may be increased or portions of the region may be ignored.

In some embodiments, the region may be determined based at least in part on the repetitive nature of the selected features. For example, a band may have a periodic feature. The period of the feature may be used to determine bounds of the region in time and/or scale.

The size, shape, and location of the one or more regions may also be adaptively manipulated using signal analysis. The adaptation may be based at least in part on changing characteristics of the signal or features within the various domain spaces.

As a signal is being processed, for example by processor 412, the region may be moved over the signal in any suitable domain space over any suitable parameter in order to determine the value or change in value of the selected features. The processing may be performed in real-time or via a previously recorded signal. For example, a region may move over the breathing band in the time-scale domain over time. When the selected features have been analyzed, they may be correlated with effort over time, and hence show the value or change in value of effort over time.

In some embodiments, the determined effort may be provided as a quantitative or qualitative value indicative of effort. The quantitative or qualitative value may be determined using the value or change in values in one or more suitable metrics of relevant information, such as the selected features mentioned above. The quantitative or qualitative values may be based on an absolute difference from a baseline or a calibrated value of the features. For example, breathing effort of a patient may be calibrated upon initial setup. Alternatively, the values may be indicative of a relative change in the features such as the change in distance between peaks in amplitude, changes in magnitude, changes in energy level, or changes in the modulation of features.

The quantitative or qualitative value of effort may be provided to be displayed on a display, for example on display 28. Effort may be displayed graphically on a display by depicting values or changes in values of the determined effort or of the selected features described above. The graphical representation may be displayed in one, two, or more dimensions and may be fixed or change with time. The graphical representation may be further enhanced by changes in color, pattern, or any other visual representation.

The depiction of effort through a graphical, quantitative, qualitative representation, or combination of representations may be presented on output 414 and may be controlled by processor 412.

In some embodiments, a display and/or speaker on output 414 may be configured to produce visual and audible alerts, respectively, when effort rises above or falls below some quantitative or qualitative threshold value. Visual alerts may be displayed on, for example, display 28 and audible alerts may be produced on, for example, speaker 22. The threshold value may be based at least in part on empirical data, baseline readings, average readings, or a combination of data. The threshold value may be configured at the start of operation or configured during operation. In some embodiments, processor 412 may determine whether or not to produce visual, audible, or combination of alerts. The alerts may be triggered if effort rises above or falls below the threshold value by a particular percentage change or absolute value change.

The analysis performed above that leads to a value of determined effort and/or an alert may also be used to detect events based at least in part on determined effort and/or other detected features. For example, this process may be used in connection with sleep studies. Increased effort may be used to detect and/or differentiate apneic events from other events. For example, reduced effort may indicate a central apnea and increased effort may indicate an obstructive apnea. In an embodiment, respiration effort from a PPG signal may be used in combination with other signals typically used in sleep studies. In one embodiment, the present disclosure may be used to monitor the effect of therapeutic intervention, for example, to monitor the effect of asthmatic drugs on a patient's respiratory effort. For example, a patient's respiratory effort may be monitored to determine how quickly the patient's respiratory effort reduces over time, if at all, after the patient receives a drug to relieve the symptoms of asthma.

Figure 5:
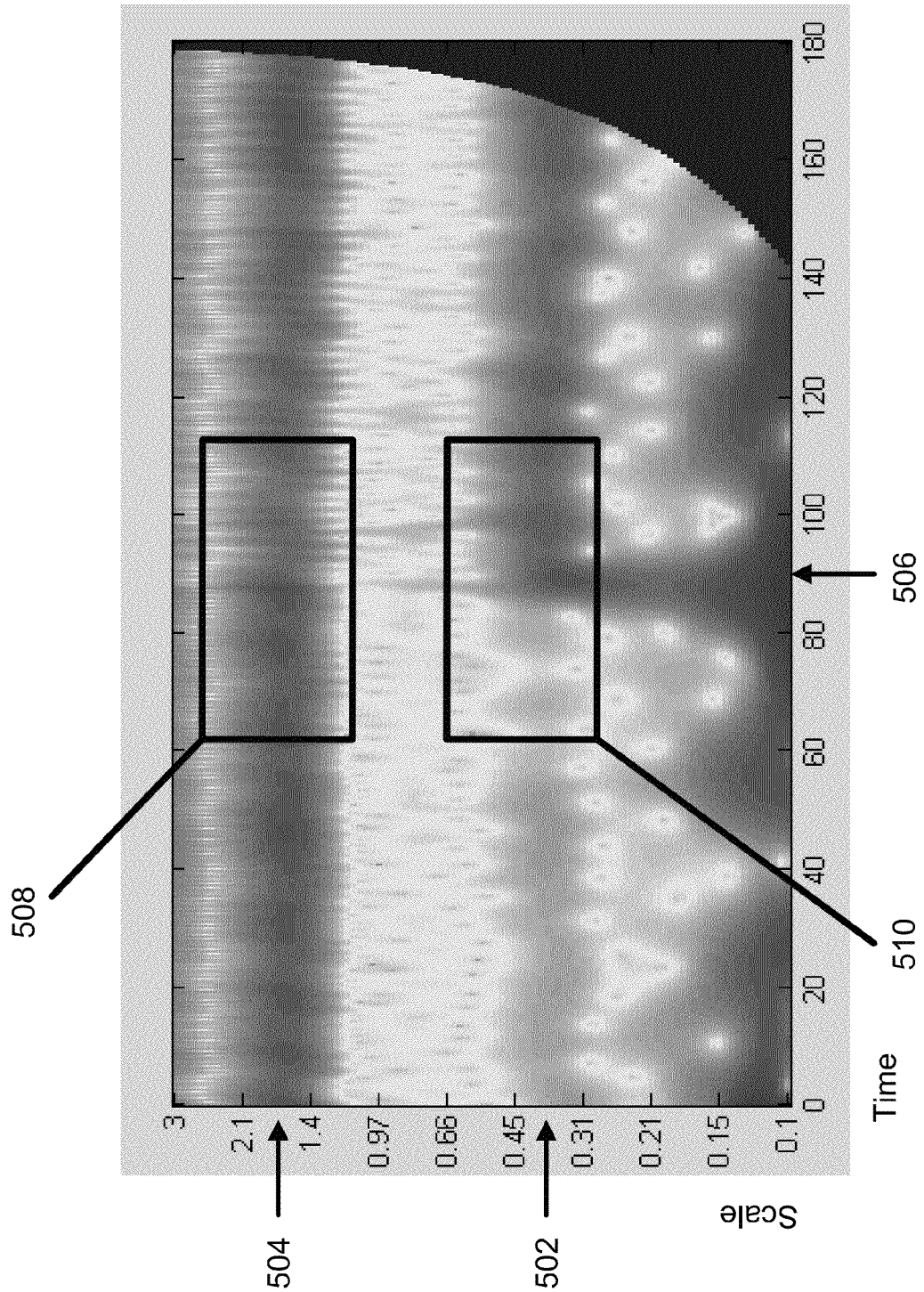
FIG. 5 is an illustrative scalogram showing the manifestation of a plurality of bands and an increase in effort in accordance with some embodiments.

FIG. 5 shows an illustrative scalogram of a PPG signal that may be analyzed in accordance with an embodiment of the disclosure. The scalogram may be produced by system 10 of FIGS. 1 and 2 or system 400 of FIG. 4 as described above. The scalogram as shown includes breathing band 502 and pulse band 504. These bands may be found and analyzed for features that may be indicative of breathing effort.

FIG. 5 shows an increased respiratory effort beginning at time 506, which may be caused by a patient experiencing increased breathing resistance. In order to detect this change in respiration effort, regions 508 and 510 may be used. Region 508 is generally located over a portion of pulse band 504 and region 510 is generally located over a portion of breathing band 502. Regions 508 and 510 may be shifted across the scalogram over time, allowing the features within the regions to be analyzed over time. The size, shape, and locations of regions 508 and 510 are merely illustrative. The features of the regions may be changed as they are shifted and any other suitable size, shape, and location may be used as described above.

At time 506, it may be observed that the modulation of the amplitude and scale of pulse band 504 may begin to increase (e.g., within region 508). Analysis of this modulation or change of this modulation, as described above, may be correlated to the patient's breathing effort because increased respiration effort may lead to this increase in amplitude and scale modulation of the pulse band. The modulation may be determined by analyzing, for example, the modulation of the ridge of the pulse band.

Increased respiration effort may also lead to increased amplitude and energy of the breathing band 502. The increase in amplitude and energy can be seen within region 510 at time 506. The amplitude may be determined by analyzing the ridge of the respiration band. The energy may be determined by analyzing the average or median energy within region 510. Analysis of the amplitude and/or energy or change in amplitude and/or energy within region 510 may also be correlated to the patient's breathing effort.

The patient's breathing effort may be determined based at least in part on the amplitude modulation, scale modulation, the amplitude, or the energy of the respiration band or the pulse band, or changes in those features, or any suitable combination thereof.

It will be understood that the above techniques for analyzing a patient's breathing effort can be used to determine any kind of effort. For example, these techniques can be used to determine the effort associated with any biological process, mechanical process, electrical process, financial process, geophysical process, astronomical process, chemical process, physical process, fluid process, speech process, audible process, meterological process, and/or any other suitable process, and/or any combination thereof.

As an additional example, the above techniques may be used to determine effort in a mechanical engine. Engine function may be monitored and represented using signals. These signals may be transformed and represented by, for example, a scalogram. Normal engine function may produce a band or bands within the scalogram. Features of this band or bands may change or become apparent as the engine exerts more or less effort. These features may include changes in the amplitude modulation, scale modulation, the amplitude, or energy of the bands. These features may also change or become apparent in other regions of the scalogram. The appearance or change in these features may then be correlated to effort or change in effort exerted by the engine.

It will also be understood that the above techniques may be implemented using any human-readable or machine-readable instructions on any suitable system or apparatus, such as those described herein.

Figure 6:
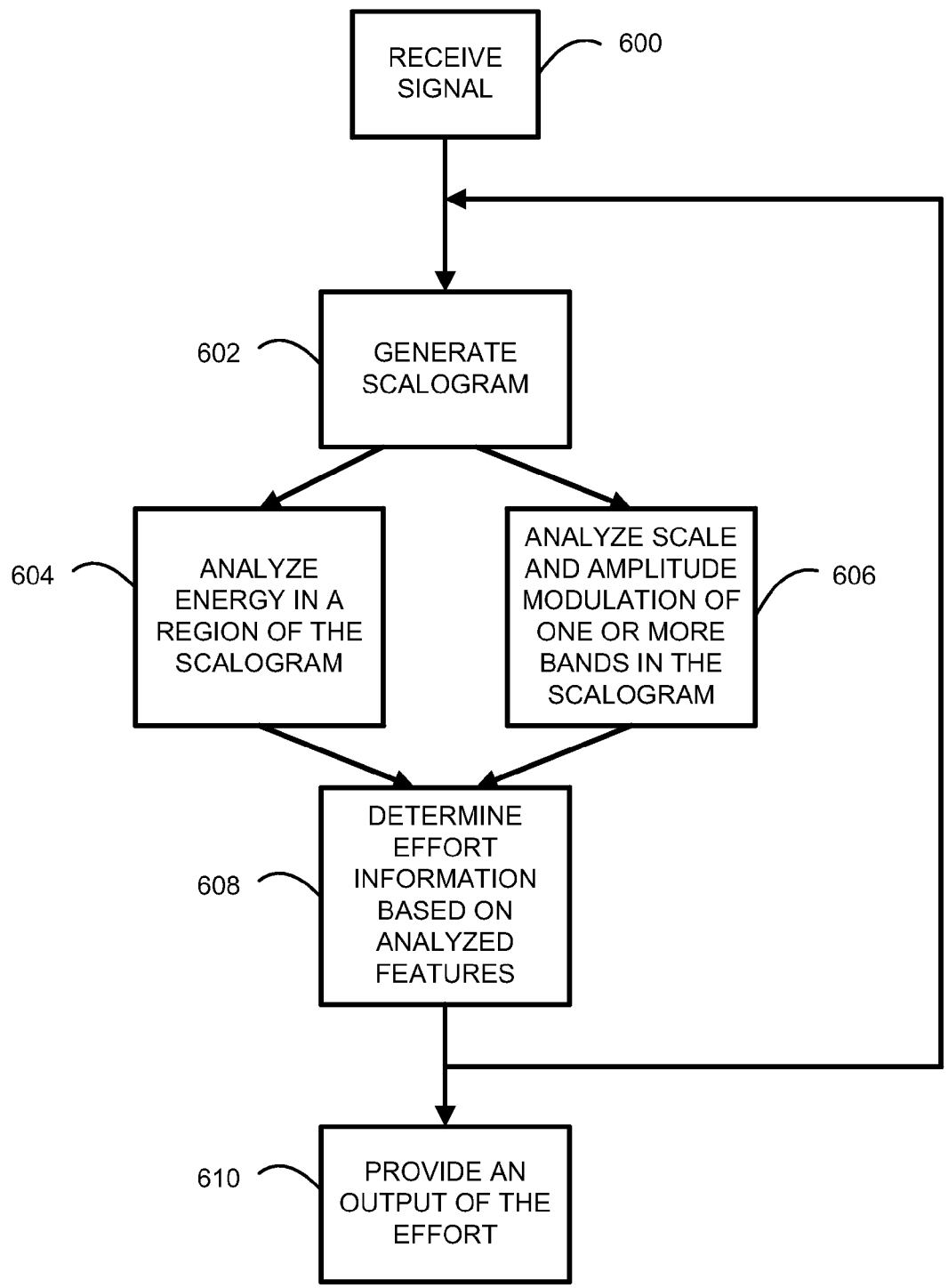
FIG. 6 is an illustrative flow chart depicting the steps used to determine effort in accordance with some embodiments.

FIG. 6 is an illustrative flow chart depicting the steps that may be used to determine effort. In step 600, one or more signals may be received, including, for example, one or more biosignals (e.g., electrocardiogram, electroencephalogram, electrogastrogram, electromyogram, heart rate signals, pathological sounds, ultrasound, or any other suitable biosignal), physiological signals, dynamic signals, non-destructive testing signals, condition monitoring signals, fluid signals, geophysical signals, physical signals, astronomical signals, electrical signals, electromagnetic signals, mechanical signals, financial signals including financial indices, sound and speech signals, chemical signals, meteorological signals including climate signals, and/or any other suitable signal, and/or any combination thereof. As an illustrative example, the input signal may be a PPG signal.

In step 602, the received signal(s) may be transformed into any suitable domain, such as a Fourier, wavelet, spectral, scale, time, time-spectral, or time-scale domain. For example, the signal(s) may be transformed into a time-scale domain using a wavelet transform such as a continuous wavelet transform. Once the signal is transformed into a suitable domain, it may be depicted by a suitable representation. Suitable representations may include two-dimensional or three-dimensional representations. As an illustrative example, the signal transformed into the time-scale domain and then may be represented by a scalogram.

Once the signal is transformed and represented by a suitable representation, one or more features may be analyzed within the signal representation as shown in steps 604 and 606. In steps 604 and 606, one or more regions within the signal representation may be chosen for inspection. These regions may be similar to region 508 and region 510. As stated above with respect to region 508 and region 510, the regions may be comprised of any suitable size, shape, and location. They also may be shifted across the scalogram over time, allowing features within the regions to be analyzed over time. For example, the regions may cover bands within a scalogram such as a pulse band or a respiration band. The regions may also cover any other suitable bands or features within the signal representation.

In step 604, the features analyzed within a region may include amplitude or energy. In step 606, amplitude modulation, scale or frequency modulation, distances between peaks, and/or any other suitable features and/or combination of features may be analyzed.

In step 608, effort information may be determined based at least in part on the analysis of the features in steps 604 and 608. As described above with respect to FIG. 5, effort may be correlated with changes or the appearance of the features found and analyzed in steps 604 and 606. For example, breathing effort may be correlated with a change or weighted change in amplitude, energy, amplitude modulation, frequency modulation, and/or scale modulation in the breathing and/or pulse bands. The correlation between effort and the analyzed features may be used to determine quantitative or qualitative values associated with effort. The determined values may, for example, indicate effort or a change of effort. The values may be determined based at least in part on an absolute or percentage difference from a baseline or calibrated value of effort. Furthermore, the values may be determined based at least in part on changes or appearance of the analyzed features within the signal representation.

The analysis performed in step 608 may also determine whether the determined effort has risen above or fallen below a threshold value. The threshold value may be based at least in part on empirical data, baseline readings, average readings, or a combination of data. The threshold value may be configured based at least in part on effort or features at the start of operation or may be adjusted during operation. If effort crosses a threshold value, an alert may be issued. In some embodiments, the alert may be triggered if effort rises above or falls below a threshold value by a particular percentage change, absolute value change, or if the determined effort value crosses the threshold value.

The analysis performed in step 608 may also detect events based at least in part on determined effort and/or other detected features. For example, this process may be used in connection with sleep studies. Increased effort may be used to detect and/or differentiate apneic events from other events. If such an apneic event occurs, an additional notification may be generated. In an embodiment, respiration effort from a PPG signal may be used in combination with other signals typically used in sleep studies.

In step 610, the signal analysis and determined effort may be output along with a possible alert if an alert has been triggered. The output may be displayed on a display, such as display 28 shown in FIG. 1. A graphical display may be generated based at least in part on the determined qualitative or quantitative values representing effort or changes in effort. The graphical representation may be displayed in one, two, or more dimensions and may be fixed or change with time. The graphical representation may be further enhanced by changes in color, pattern, or any other visual representation. Additionally, the alert may be made visual by being displayed on a display, for example display 28, or may be made through an audible sound on a speaker, for example speaker 22.

As the signal analysis and determined effort are being output in step 610, the whole process may repeat. Either a new signal may be received, or the effort determination may continue on another portion of the received signal(s). The process may repeat indefinitely, until there is a command to stop the effort determination, and/or until some detected event occurs that is designated to halt the effort determination process. For example, it may be desirable to halt effort determination after a sharp increase in breathing effort is detected.

It will also be understood that the above method may be implemented using any human-readable or machine-readable instructions on any suitable system or apparatus, such as those described herein.

From the foregoing disclosure it will be appreciated that respiratory effort manifests itself in the scalogram of a photoplethysmograph ("PPG") signal as an increase in the energy content of the respiratory features within the scalogram derived from the PPG signal. This respiratory effort information can be extracted from the scalogram and used to flag respiratory events or certain characteristics of respiratory events or activities. For example, we turn now to ways in which various measures can be derived from the effort signal alone or in conjunction with other signals from the patient in order to characterize certain physiologic attributes of the patient. These characterizations are useful in assessment of the patient and/or to guide treatment of the patient.

Figure 7:
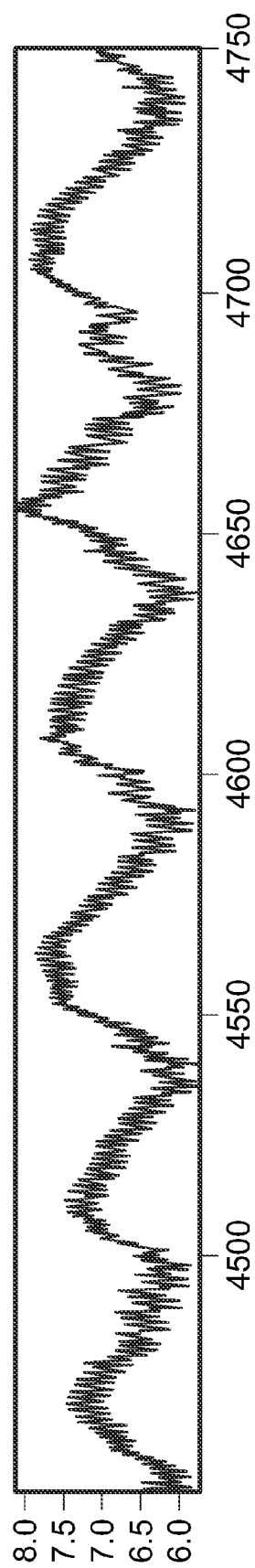
FIG. 7 is an illustrative example of a patient monitor signal waveform that includes signal information content indicative of the effort a patient is exerting in order to breathe.

FIG. 7 shows an example of a PPG electrical signal from a patient who suffers from sleep apnea and who is undergoing a sleep laboratory study. Time progresses from left to right across FIG. 7.

Figure 8:
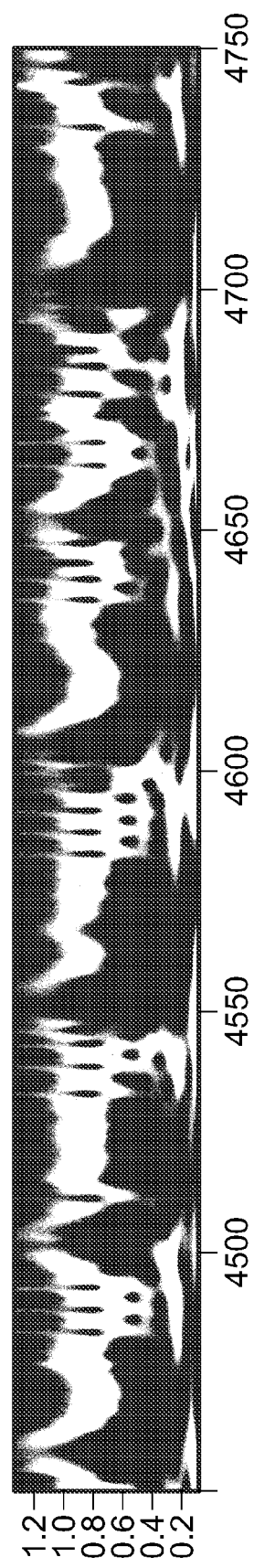
FIG. 8 is an illustrative scalogram of the FIG. 7 patient monitor signal.

FIG. 8 is a scalogram (electrical signals) of the FIG. 7 PPG signal. FIG. 8 is plotted against the same time scale as FIG. 7, and both plots are shown synchronized with one another.

Figure 9:
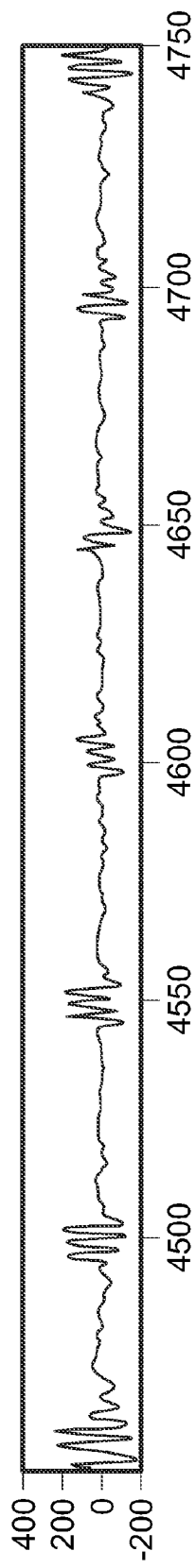
FIG. 9 is an illustrative signal waveform from a breath or breathing air flow monitor that is coupled to a patient.

FIG. 9 is a plot of patient airflow (as captured in an airflow electrical signal), which shows regions of respiration activity (where the plot has relatively large up and down excursions) and regions of apnea (where the plot has relatively small excursions). Again, FIG. 9 is plotted against the same time scale as, and is synchronized with, FIGS. 7 and 8.

Figure 10:
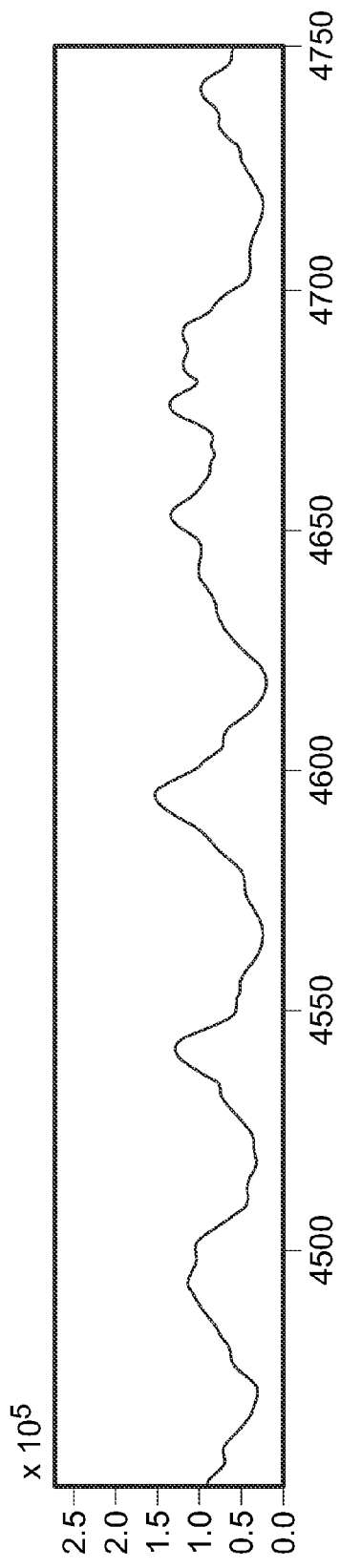
FIG. 10 is a simplified waveform of a respiratory effort signal derived from the FIG. 8 scalogram. All of FIGS. 7-10 are plotted against the same horizontal time scale, and all are synchronized with one another.

FIG. 10 is a plot of a breathing effort electrical signal derived from information in the scalogram (FIG. 8). Once again, FIG. 10 is plotted against the same time scale as, and is synchronized with, FIG. 7-9. As described earlier in this disclosure, the FIG. 10 effort signal may be derived in a variety of ways from the scalogram. In this example, the scalogram values have been summed across a region of scales corresponding to those associated with a range of normal respiratory activity. The scalogram in this example is composed of the transform modulus values.

Figure 11:
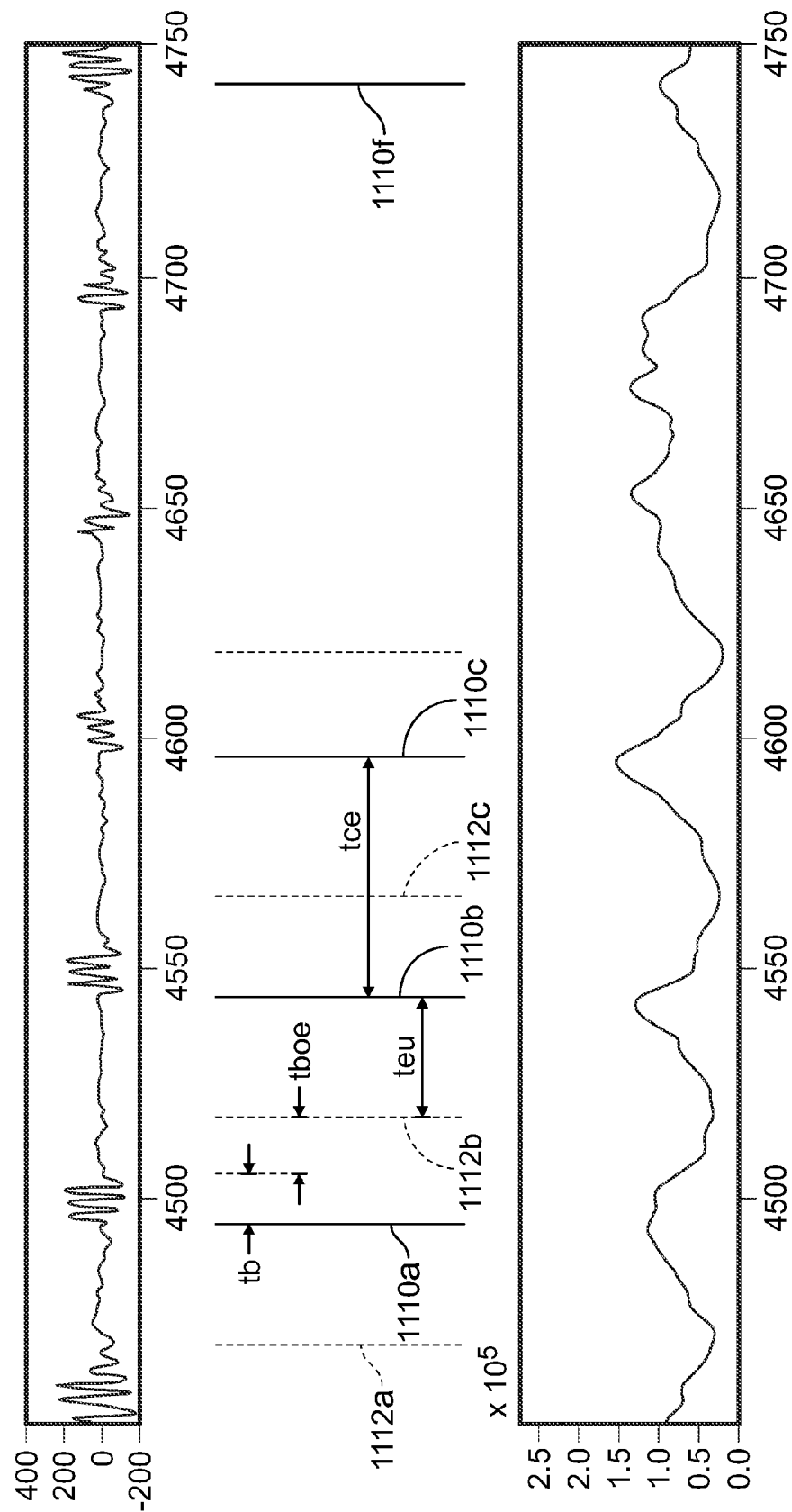
FIG. 11 is a reproduction of FIGS. 9 and 10 with the addition of some representative reference marks and symbols that are useful in explaining certain aspects of the disclosure.

From FIG. 10 one can see a distinct pattern to the effort signal. This pattern takes the form of generally increasing effort (each upward-sloping portion of the effort signal), followed by decreasing effort (downward-sloping portions of the effort signal). This cycle repeats at the same rate as the occurrence of airflow regions in the airflow signal (FIG. 9). Comparing FIGS. 9 and 10 one can see that the peaks of the effort features generally coincide with the initiation of patient respiration as shown in the airflow signal. This is shown in more detail in the annotated versions of FIGS. 9 and 10 that are provided in FIG. 11. For example, solid vertical lines 1110a, b, c, etc. show how each peak in the effort signal typically coincides with start of more effective breathing by the patient. The curve features and inter-relationships shown in FIG. 11 are indicative of the patient gradually increasing his or her respiratory effort during an apneic event (upward sloping effort curve) until there is patency of the airway, allowing the flow of air to and from the lungs to take place (area of larger excursions in the airflow curve). Once respiratory airflow activity is established (as indicated in the airflow signal by the distinct, large-amplitude oscillations), the effort signal is seen to reduce (downward sloping effort curve).

A number of respiratory characteristics can be extracted from the PPG effort signal alone or in conjunction with other signals collected from the patient. Some examples of these are indicated in FIG. 11 and are as follows.

One such respiratory characteristic is the time from the initiation of an upstroke to the peak of the effort feature (teu in FIG. 11).

Another respiratory characteristic is the ratio of teu to the total apnea cycle time (tce in FIG. 11) from the effort signal. (In the various ratios mentioned throughout this disclosure, each of the numerator and denominator may sometimes be referred to as a precursor to the ratio.)

Still another respiratory characteristic is the ratio of some characteristic effort (e.g., maximal effort) to some characteristic time (e.g., teu), again from the effort signal. Such a ratio provides a characteristic rate of effort increase.

Yet another respiratory characteristic is the time taken from the end of breathing until effort begins to increase (tboe in FIG. 11). During this period the patient has not yet attempted to breathe against the apneic condition. This respiratory characteristic may be derived from features of the airflow and effort curves.

Still another respiratory characteristic is the ratio of tboe to total cycle time tce, or the ratio of tboe to respiration time (tb from the airflow curve in FIG. 11), or the ratio of tboe to some other time.

Yet another respiratory characteristic is the ratio of maximum effort to minimum effort occurring within one effort feature cycle in the effort signal. This may be indicative of the relative effort required by the patient to begin respiration.

Figure 12:
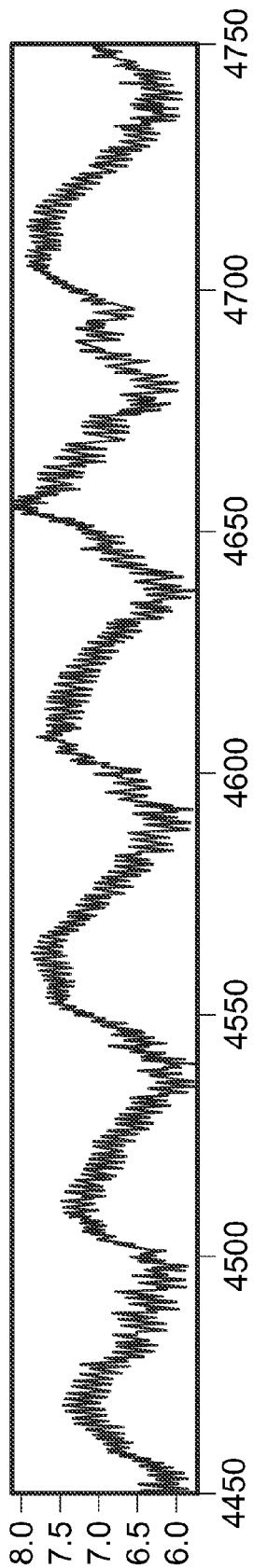
FIG. 12 reproduces FIG. 7 in time synchronization with a different scalogram of that signal as shown in FIG. 13.
Figure 13:
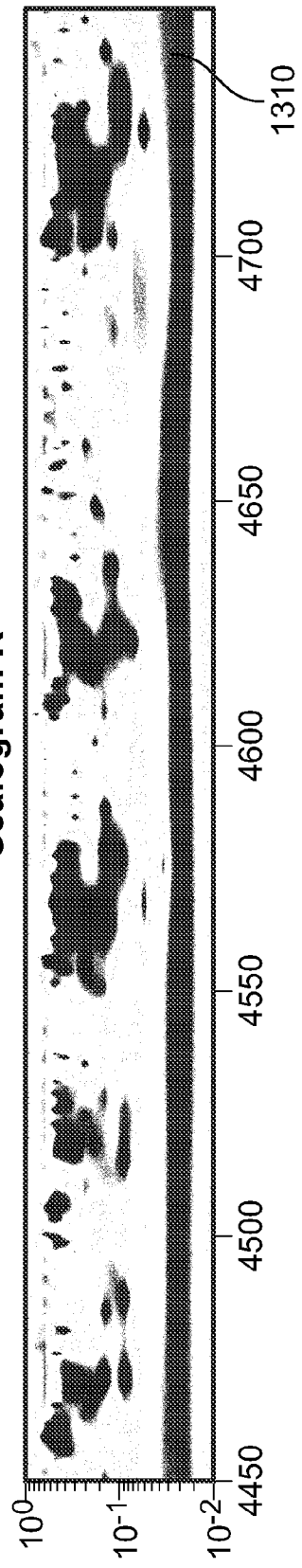
FIG. 13 is another illustrative scalogram of the FIG. 12 patient monitor signal.

By expanding the range of scales used to produce the scalogram (e.g., FIG. 8) of the PPG signal (e.g., FIG. 7), it can be possible to detect an apnea band in the scalogram. This is shown in FIGS. 12 and 13, the first of which repeats the PPG signal from FIG. 7, and the second of which shows a scalogram of the FIG. 12 signal employing a range of scales that is sufficiently expanded to show apnea band 1310 in the scalogram. Apnea band 1310 is caused by the large-scale repeating baseline cycle in the PPG signal at scales of the order of magnitude of the apnea features. Thus another measure of relative effort (somewhat like what is mentioned in the immediately preceding paragraph) may be a ratio of a characteristic of the respiratory features in the scalogram to the energy in the apnea features (e.g., from apnea band 1310).

Consideration may also be given to the pulse band in the scalogram. The excursions of the pulse band in scale may be indicative of the amount of effort that a patient is exerting in an attempt to breathe, or during breathing. Thus a measure of the variation (range) of the pulse band scales may be indicative of respiratory effort. The excursions, caused by short-duration heart rate increases, may also be indicative of patient distress or patient arousal. The amplitude of the pulse band (e.g., reduced amplitude associated with increased pulse rate) may also be considered as a measure of respiratory effort.

The above breathing characteristics are only exemplary and indicative of a wide range of parameters that may be derived using the PPG effort signal and other patient indicia.

As yet another example, an autocorrelation of the effort signal (e.g., FIG. 10 or lower curve in FIG. 11) may provide a way to derive another time parameter that may be called the apnea periodicity.

Those skilled in the art will recognize that the present methods and apparatus may also be implemented with effort signals derived from the PPG signal using aspects of the scalogram transform other than the modulus. For example, the real or imaginary part of the transform may be used, or a rescaled scalogram may be used, or some power of the modulus may be used (e.g. the squared modulus (corresponding to an energy representation).

Those skilled in the art will also recognize that the present methods and apparatus alternatively be used with effort signals derived from other transforms and other two-dimensional signal representations. Those skilled in the art will still further recognize that the present methods and apparatus may also be used with other signals that contain signal indicia indicative of respiratory or other effort. For example, other illustrations of apparatus suitable for monitoring a patient's breathing effort and producing patient monitor signals indicative of such effort include piezo-bands (one such band around the patient's chest, and another such band around the patient's abdomen), transthoracic impedance measurement across electrocardiogram ("ECG" or "EKG") electrodes on the patient's chest, etc.

FIGS. 14*a-f* (sometimes referred to collectively as FIG. 14) show an illustrative embodiment of apparatus 1400 which can implement various aspects of the disclosure. To some extent, the circuit elements shown in FIG. 14 are adapted to extract, determine, and/or use particular patient breathing characteristic parameters; but it will be understood that these particular parameters may only be specific examples of the type of parameter referred to. In such cases, other specific examples of the same general type of parameter may be used or implemented instead, if desired. It will also be understood that although a human subject or "patient" 1410 is shown in FIG. 14, this is done only for completeness, and the patient is not in fact part of apparatus 1400 or this disclosure generally. Connections between the various sheets of FIG. 14 are indicated by the encircled capital letters. For example, the signal applied to encircled capital letter A in FIG. 14*a* can be used at encircled letter A in any or all of FIGS. 14*b*, 14*d*, and 14*e*.

Figure 14A:
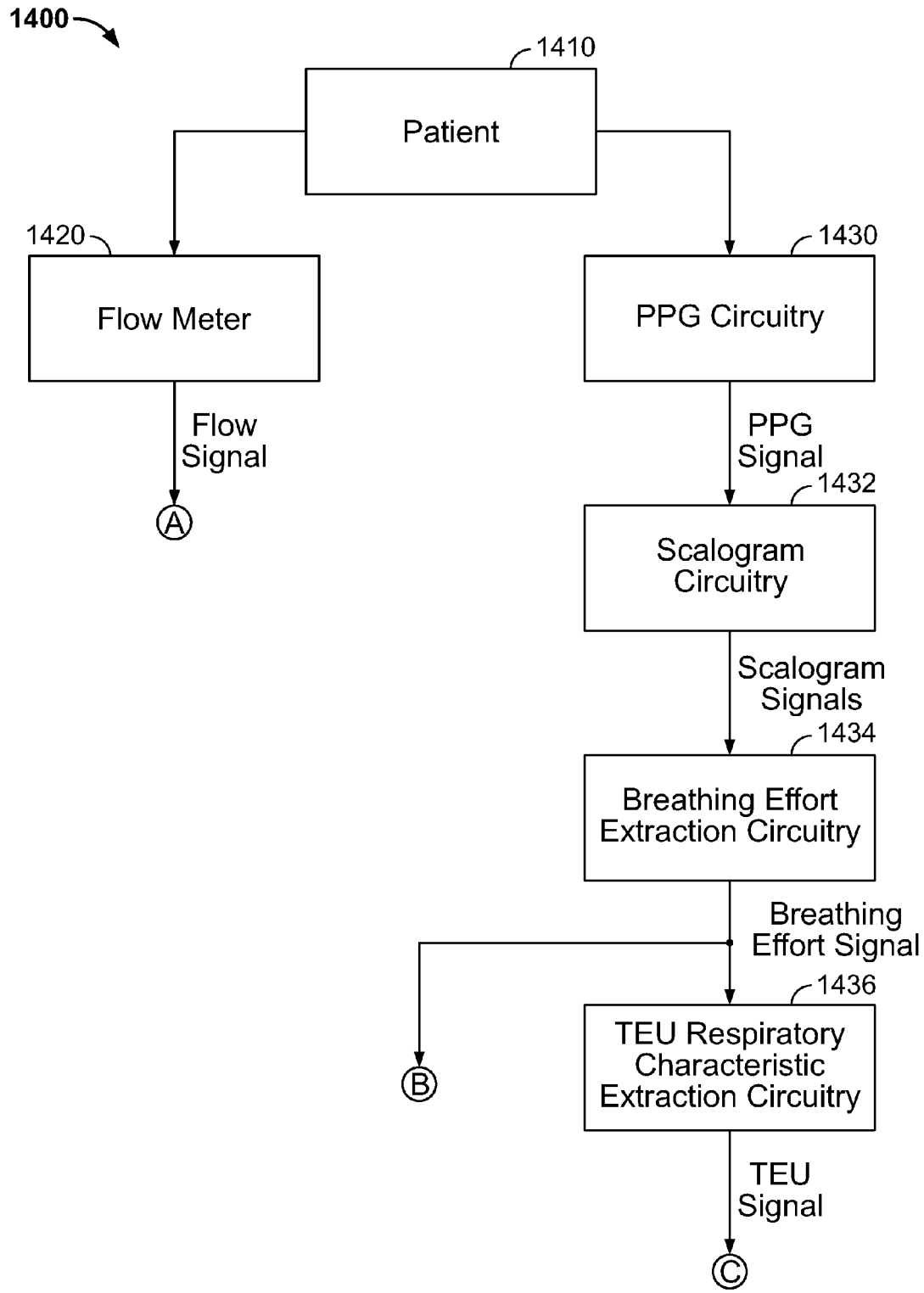
FIGS. 14a-14f (sometimes referred to collectively as FIG. 14) are simplified blocks diagrams of illustrative embodiments of apparatus in accordance with various aspects of the disclosure.
Figure 14B:
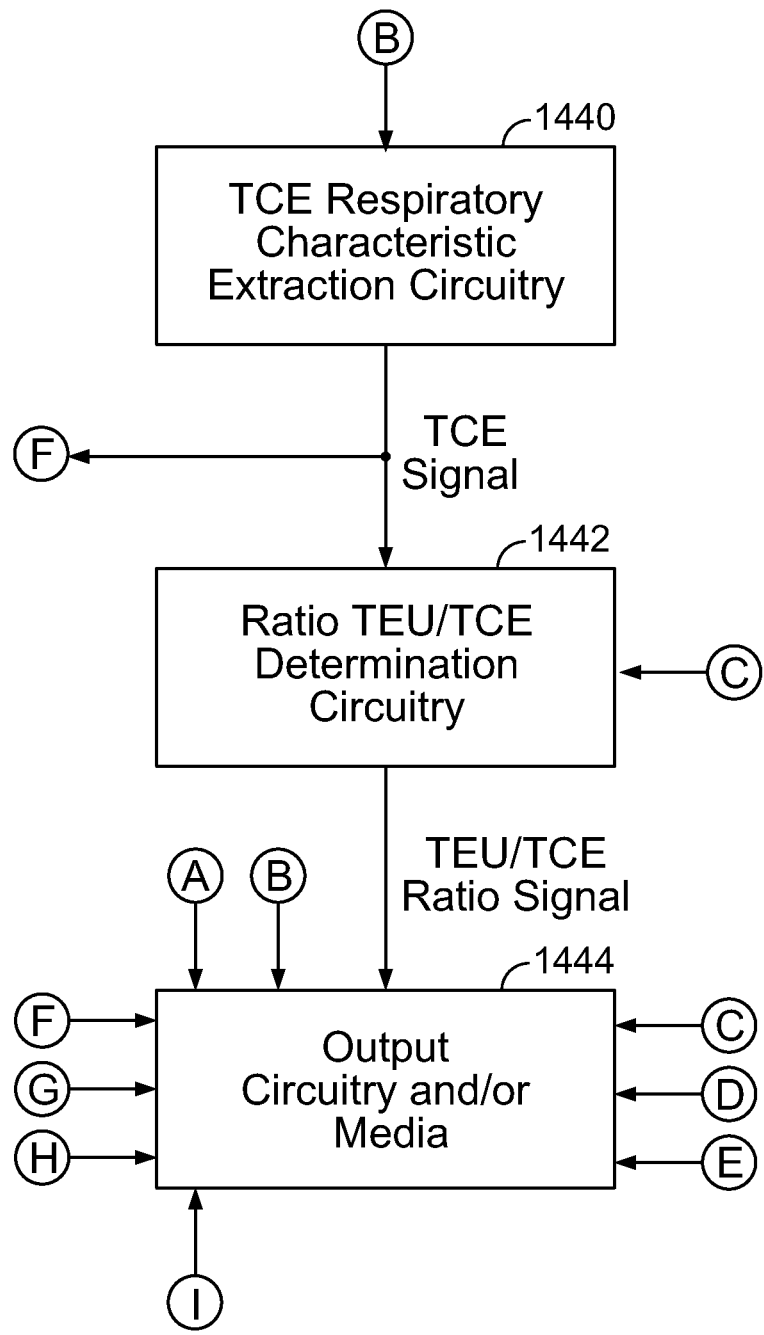

As shown in FIG. 14*a*, patient 1410 may be coupled to flow meter apparatus 1420 and to PPG circuitry 1430. PPG apparatus is again used only as an example, and it will be understood that component 1430 can instead be any other apparatus for obtaining a respiratory or other effort signal from patient 1410. Flow meter 1420 may not be needed in all embodiments, but it is included on FIG. 14 as a possible element of at least some embodiments. Flow meter 1420 may be apparatus for measuring the flow of air to and from the patient's lungs as the patient breathes, and for producing a flow electrical signal indicative of the amount of such flow. An example of such a flow signal is shown in FIG. 9.

PPG circuitry 1430 may be circuitry as described elsewhere in this disclosure for producing a PPG electrical signal from the patient. An example of a PPG signal is shown in FIG. 7. This PPG signal may be applied to the scalogram circuitry 1432, which may also be as described elsewhere in this disclosure. Scalogram circuitry 1432 produces scalogram signals indicative of the PPG signal. An example of such scalogram signals is shown in FIG. 8. The scalogram signals are applied to breathing effort extraction circuitry 1434, which again may be as described elsewhere in this disclosure. Circuitry 1434 produces a breathing effort electrical signal, an example of which is shown in FIG. 10. This breathing effort signal can be used by any of a number of other components throughout FIG. 14.

One component that may use the breathing effort signal is TEU respiratory characteristic extraction circuitry 1436. Circuitry 1436 can extract the previously described teu respiratory characteristic from the breathing effort signal for a patient (see again FIG. 11, where the teu characteristic is shown). For example, circuitry 1436 may be circuitry that can detect (1) a minimum in the effort signal, (2) a subsequent maximum in the effort signal, and (3) the elapsed time teu from the occurrence of that minimum to the occurrence of that subsequent maximum. Circuitry 1436 may output a TEU electrical signal indicative of the value of the teu parameter thus determined by that circuitry. This TEU signal may be applied to the other components of the FIG. 14 apparatus. For example, the TEU signal may be applied to output circuitry and/or output media 1444. Element 1444 is preferably a means by which any signal or signals applied to it can be stored and/or rendered in human-readable form, e.g., so that an operator of apparatus 1400 can see, interpret, and/or act on the information contained in that signal or those signals. As an illustration, the operator or someone else may use this element 1444 output to help design and/or implement a treatment or therapy for patient 1410. Element 1444 may be, for example, a graphics display monitor for displaying signals as signal traces or curves (e.g., like FIG. 7), or element 1444 may be a printer or plotter for printing or plotting such information on paper. As still another example, element 1444 may be the media on which such information is stored and/or output. Thus element 1444 may be or include, e.g., electronic memory, disc memory or the like; or element 1444 may be or include a paper (or the like) print-out of the information applied to that element. While this description of element 1444 has been provided with particular reference to the TEU signal as a possible input to element 1444, it will be understood that element 1444 may be similar (and may function similarly) for all of the other inputs that element 1444 is shown as possibly receiving. Thus, for example, element 1444 may also receive the air flow signal from flow meter 1420 and/or the effort signal from circuitry 1434, and element 1444 may also output (or be the output of) either or both of those signals (e.g., as in FIG. 9 or FIG. 10, respectively).

Another component that may use the breathing effort signal (from component 1434) is TCE respiratory characteristic extraction circuitry 1440. Circuitry 1440 can extract the previously described tce respiratory characteristic from the breathing effort signal (see again FIG. 11, where the tce characteristic is shown). For example, circuitry 1440 may be circuitry that can detect (1) a maximum in the effort signal, (2) another subsequent maximum in that signal, and (3) the elapsed time tce from the occurrence of the first maximum to the second maximum. Circuitry 1440 may output a TCE electrical signal indicative of the value of the tce parameter thus determined by that circuitry. This TCE signal may be applied to other components of the FIG. 14 apparatus (one example being above-described output circuitry and/or a media 1444).

A further component that may use both the TEU and TCE signals is ratio TEU/TCE determination circuitry 1442. Circuitry 1442 can determine the ratio of the values of the teu and tce respiratory parameters that are embodied or represented by the TEU and TCE signals. Circuitry 1442 outputs a TEU/

TCE ratio electrical signal indicative of this ratio. The TEU/TCE ratio signal may be another input to above-described output and/or media 1444.

Still other components of apparatus 1400 that may use the breathing effort signal (from component 1434) are characteristic effort extraction circuitry 1450 and characteristic time extraction circuitry 1452. Characteristic effort extraction circuitry 1450 may be circuitry that can extract a desired effort characteristic value (e.g., the value of a maximum in the effort signal) from the effort signal. Circuitry 1450 outputs a characteristic effort ("EFF") electrical signal indicative of the effort parameter value it has extracted. Characteristic time ("TIME") extraction circuitry 1452 may be circuitry that can extract a desired time characteristic value (e.g., the effort increase time teu mentioned above) from the effort signal. Circuitry 1452 outputs a characteristic time ("TIME") electrical signal indicative of the time parameter value it has extracted. (If this time parameter is teu, then circuitry 1452 can be replaced by a connection from the output of element 1436.)

The output signals of elements 1450 and 1452 are applied to ratio EFF/TIME determination circuitry 1454. This circuitry can determine the ratio of the values indicated by the two signals applied to it. Circuitry 1454 outputs an EFF/TIME ratio electrical signal indicative of this ratio. The EFF/TIME ratio signal may be another input to above-described output circuitry and/or media 1444.

Figure 14C:
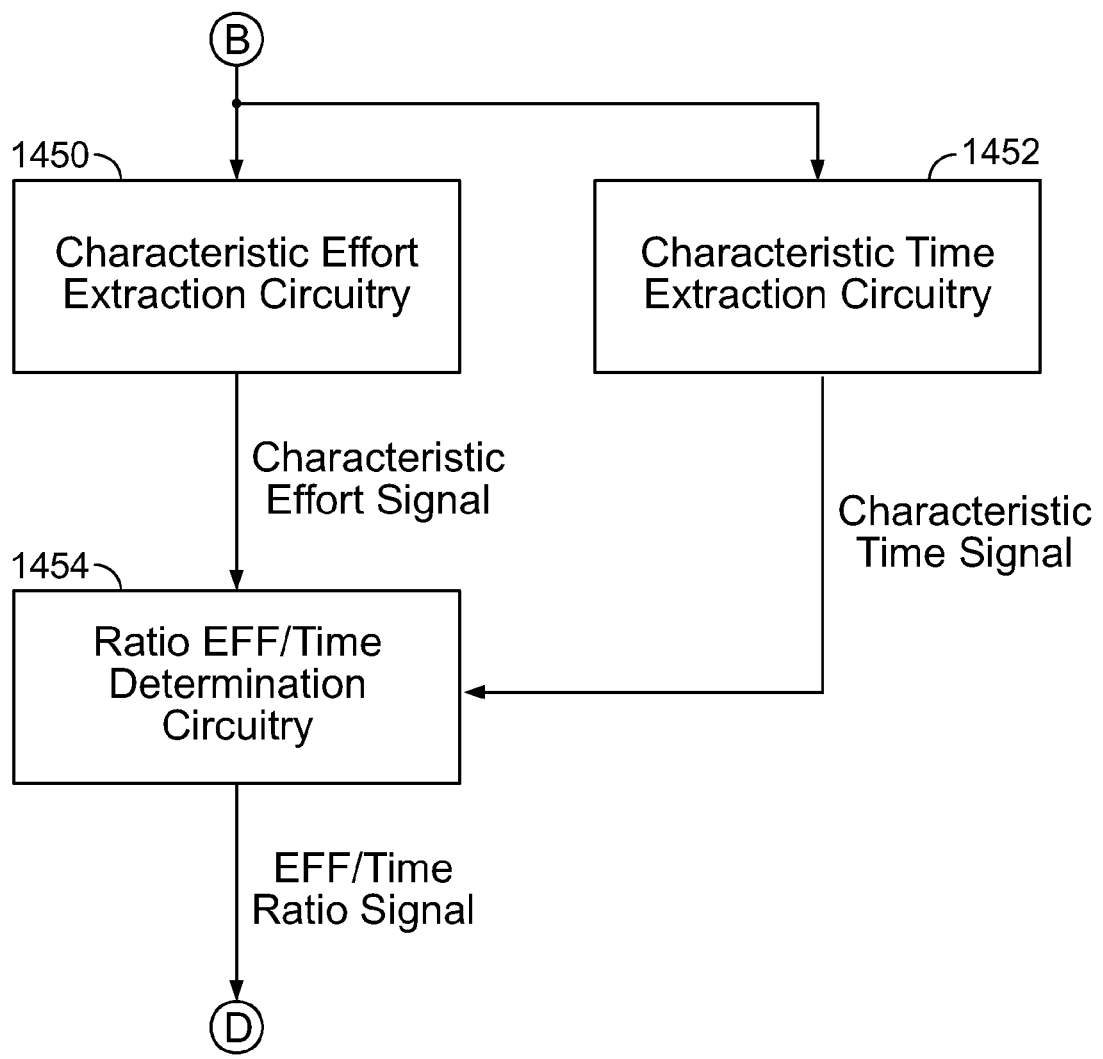
Figure 14D:
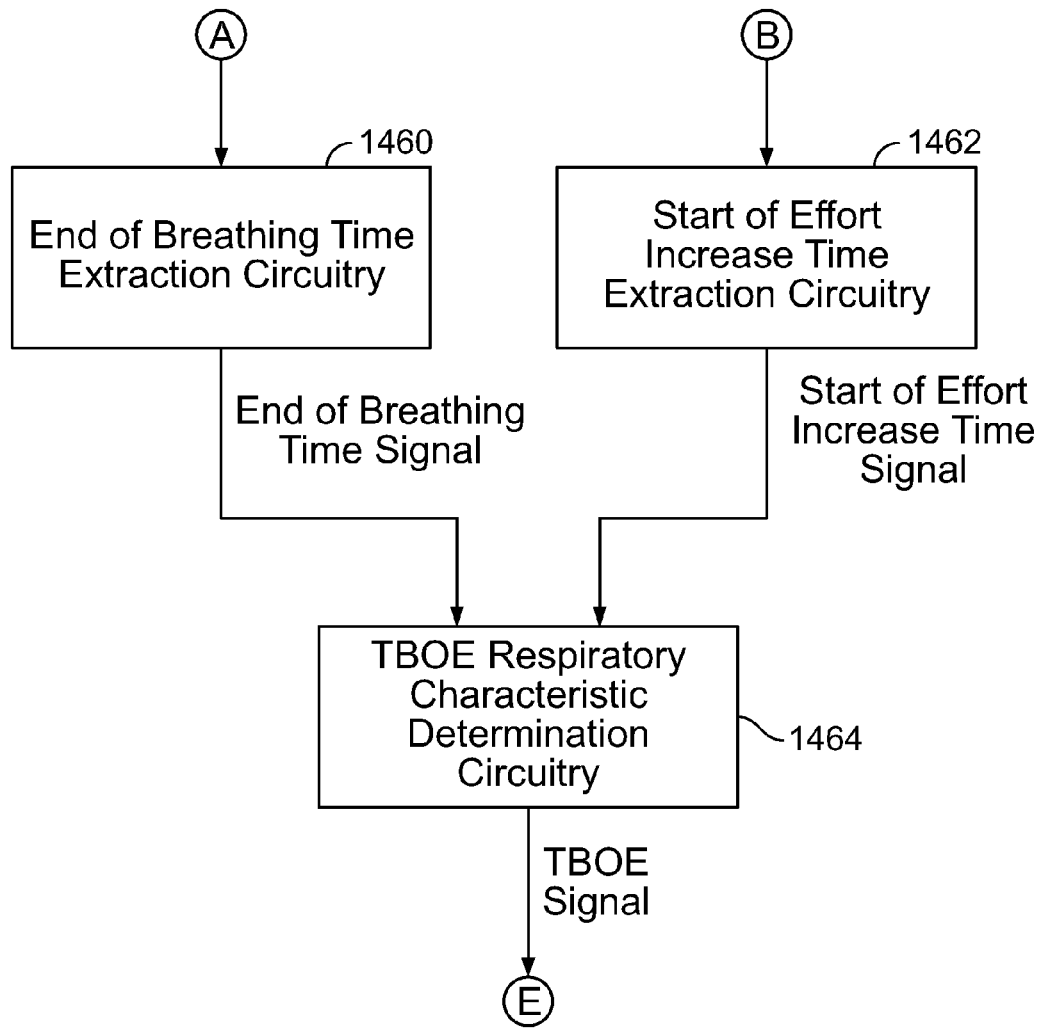

FIG. 14d shows that the flow signal (from flow meter 1420) may be applied to end of breathing time extraction circuitry 1460. This may be circuitry for analyzing the flow signal (e.g., as in FIG. 9 or the upper part of FIG. 11) to determine when effective breathing by the patient has stopped (e.g., the time when the relatively large excursion in the airflow signal stop). Circuitry 1460 outputs an end of breathing time electrical signal indicative of the breathing cessation time value it has extracted.

Also in FIG. 14d, the breathing effort signal (from element 1434) is applied to start of effort increase time extraction circuitry 1462. This may be circuitry for analyzing the effort signal to determine when a minimum value has been reached in that signal and effort has begun to increase again from that minimum. Circuitry 1462 outputs a start of effort increase time electrical signal indicative of the time parameter value it has extracted.

The output signals of elements 1460 and 1462 are applied to TBOE respiratory characteristic determination circuitry 1464. This circuitry can determine the difference between the times indicated by the two signals applied to it in order to determine above-described patient respiratory characteristics tboe (see again FIG. 11). Circuitry 1464 outputs a TBOE electrical signal indicative of the value of the tboe parameter it has determined. This TBOE signal may be another input to above-described output circuitry and/or media 1444.

Figure 14E:
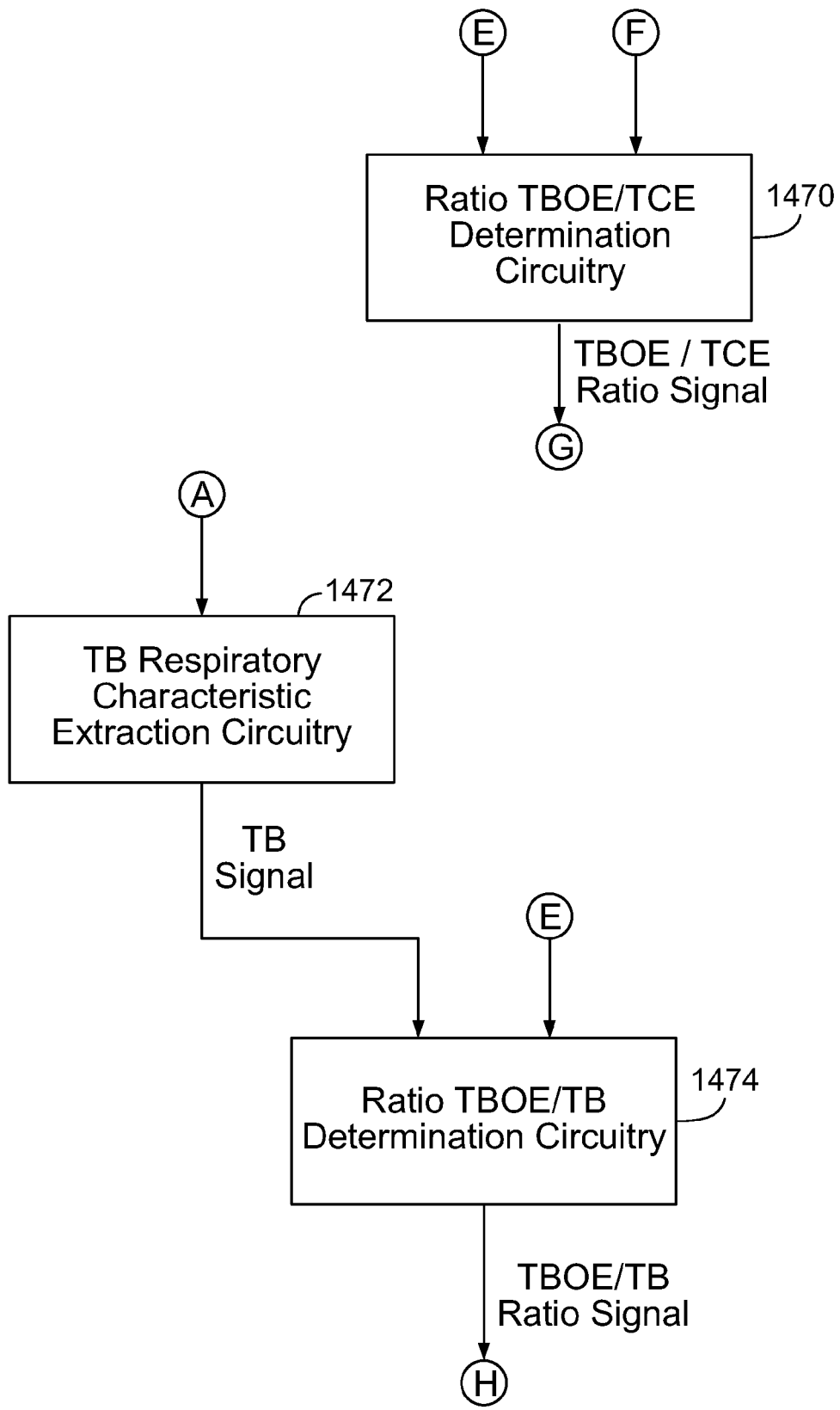

FIG. 14e shows other circuitry 1470 that may use both the TBOE signal (from element 1464) and the TCE signal (from element 1440). In particular, element 1470 is ratio TBOE/TCE determination circuitry that can determine the ratio of the tboe and tce respiratory characteristic parameter values indicated by the TBOE and TCE signals. Circuitry 1470 outputs a TBOE/TCE ratio electrical signal indicative of the above-mentioned ratio. This TBOE/TCE ratio signal may be yet another input to above-described output circuitry and/or media 1444.

FIG. 14e shows another illustrative use of the flow signal (from element 1420). This is application of the flow signal to TB respiratory characteristic extraction circuitry 1472. Circuitry 1472 may be circuitry that can extract the above-described tb breathing characteristic parameter from the flow signal (see again the upper portion of FIG. 11). For example, circuitry 1472 may be circuitry that can detect (1) the time when effective breathing by the patient starts (i.e., the start of a period of relatively large excursions in the air flow signal), and (2) the time when effective breathing by the patient subsequently ceases (i.e., the end of the period of relatively large excursions in the air flow signal. Circuitry 1472 can then output a TB electrical signal indicative of the difference between these two times.

FIG. 14e further shows the above-mentioned TB signal being applied to circuitry 1474, along with the TBOE signal (from element 1464). Circuitry 1474 may be circuitry that can determine the ratio between the values of the tboe and tb parameters indicated by the TBOE and TB signals applied to that circuitry. Circuitry 1474 outputs a TBOE/TB ratio electrical signal indicative of the tboe/tb ratio it has determined. This TBOE/TB ratio signal may be still another input to above-described output circuitry and/or media 1444.

Figure 14F:
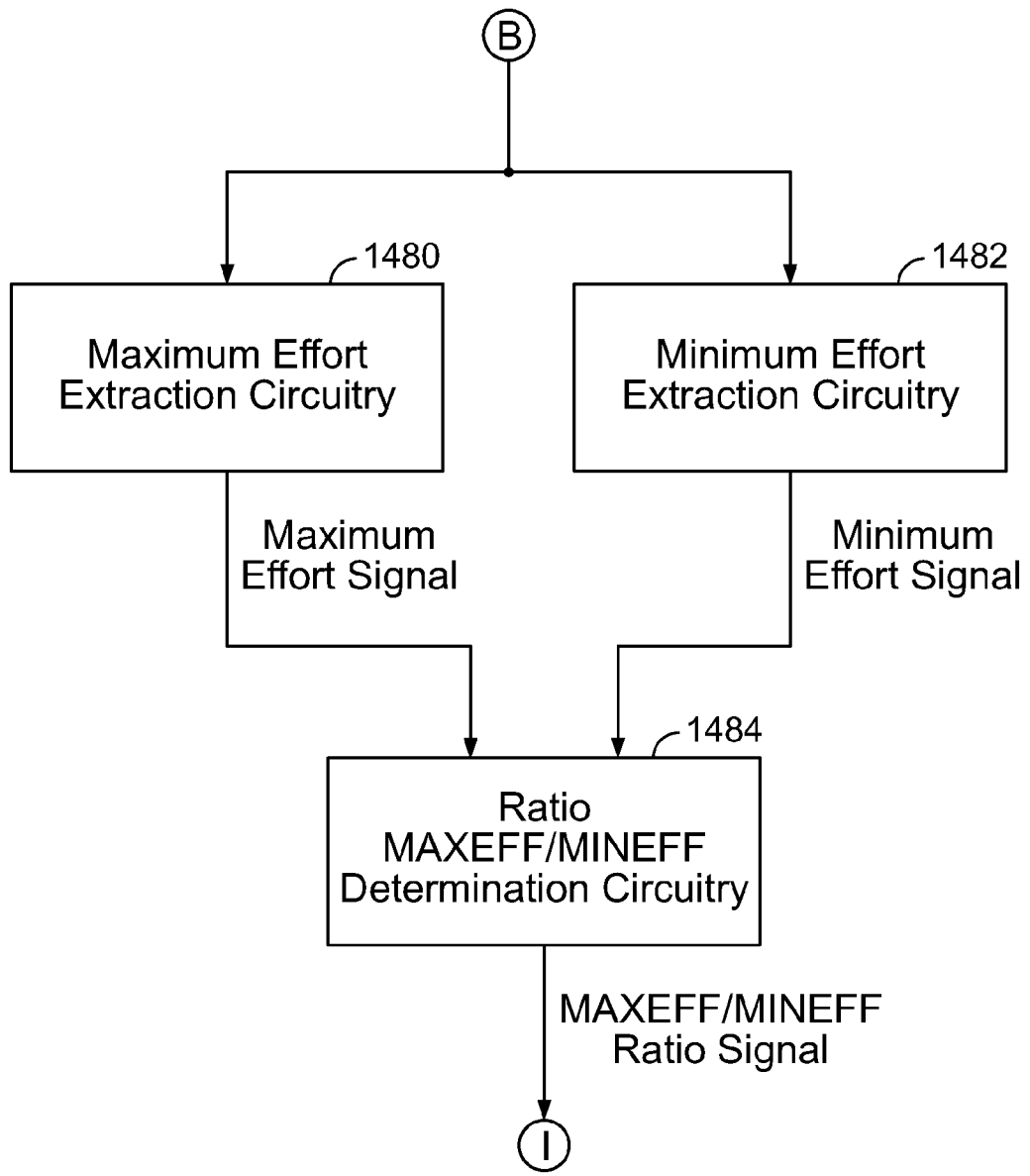

Still more illustrative components of apparatus 1400 that may use the breathing effort signal (from component 1434) are shown in FIG. 14f. These are maximum effort extraction circuitry 1480 and minimum effort extraction circuitry 1482. Circuitry 1480 may be circuitry that can (1) extract the value of a maximum in the effort signal, and (2) produce a maximum effort electrical output signal indicative of that maximum value. Circuitry 1482 may be circuitry that can (1) extract the value of a minimum in the effort signal, and (2) produce a minimum effort electrical output signal indicative of that minimum value.

The output signals of elements 1480 and 1482 are applied to ratio MAXEFF/MINEFF determination circuitry 1484. This circuitry can determine the ratio of the values indicated by the two signals applied to it. Circuitry 1484 outputs a MAXEFF/MINEFF ratio electrical signal indicative of the above-mentioned ratio. The MAXEFF/MINEFF ratio signal may be another input to above-described output circuitry and/or media 1444.

Illustrative methods or procedures in accordance with the disclosure are shown FIGS. 15a-15i (which may sometimes be referred to collectively as FIG. 15). It will be understood that not all parts of FIG. 15 are needed or employed in all embodiments. Rather, various embodiments may use or employ only certain parts of what is shown in FIG. 15.

Figure 15A:
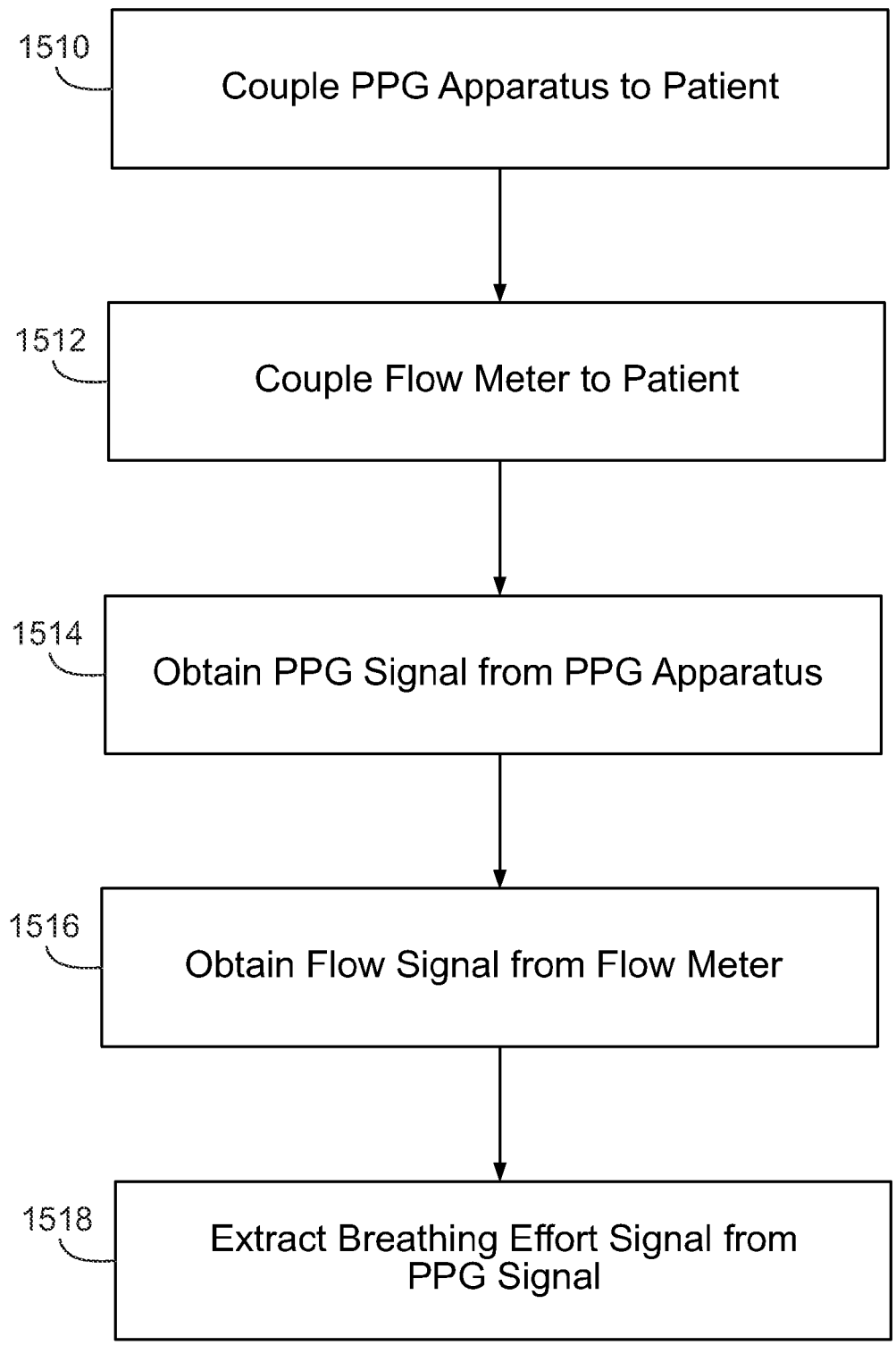
FIGS. 15a-15i (sometimes referred to collectively as FIG. 15) are simplified flow charts of illustrative embodiments of methods in accordance with various aspects of the disclosure.

In step 1510, PPG apparatus (e.g., 1430 in FIG. 14) is coupled to a patient (e.g., 1410 in FIG. 14). In step 1512, breathing air flow meter apparatus (e.g., 1420 in FIG. 14) may be coupled to the patient. Step 1512 may not be needed in all embodiments, but it is shown in FIG. 15a for completeness. In step 1514, a PPG signal (e.g., as in FIG. 7) is obtained from the PPG apparatus. In step 1516, a flow signal (e.g., as in FIG. 9) may be obtained from the flow meter apparatus. Again, step 1516 may not be needed in all embodiments, but it is shown in FIG. 15a for completeness. In step 1518, a breathing effort signal (e.g., as in FIG. 10) is extracted from the PPG signal.

As a general matter, the disclosure may involve extracting from the effort signal a respiratory characteristic signal for the patient that is based on at least one amplitude feature of the effort signal and a relative time of occurrence of that amplitude feature. Throughout this disclosure the amplitude of a signal is shown in the vertical axis in FIGS. like FIGS. 7, 9, and 10. Greater amplitude is higher in the vertical direction (or a greater amount of vertical signal excursion) in such signal depictions. The time, relative time, or elapsed time for a signal is shown on the horizontal axis in FIGS. like FIGS. 7, 9, and 10. Time increases toward the right in such signal depictions. An example of an "amplitude feature" (e.g., in the effort signal like FIG. 10) is a point at which the amplitude of that signal ceases a generally downward trend and instead begins a generally upward trend. Vertical reference lines 1112a, 1112b, and 1112c are drawn in FIG. 11 through examples of such amplitude turning points in the depicted effort signal. Each such point may be referred to as a minimum in the effort signal. (As used herein, "minimum" does not refer to an absolute minimum of a signal for all time, but only a local minimum or a minimum that is local to a significant portion of the signal. Thus each of lines 1112 in FIG. 11 passes through such a "minimum" in the effort signal, and there are still more such minima in that signal to the right of minimum 1112c in that FIG.)

Another example of an "amplitude feature" (e.g., in the effort signal) is a point at which the amplitude of that signal stops a generally upward trend and instead starts a generally downward trend. Vertical reference lines like 1110a, 1110b, 1110c, etc. are drawn in FIG. 11 through examples of such amplitude turning points in the depicted effort signal. Each such point may be referred to as a maximum in the effort signal. (Again, as used herein, "maximum" does not refer to an absolute maximum of a signal for all time, but only a local maximum or a maximum within a significant portion of the signal. Thus each of lines 1110 in FIG. 11 passes through a different one of several such maxima in the depicted effort signal. As in the case in the various "minima," the amplitude value of each of these various "maxima" may be somewhat different, but each is a local maximum for a significant portion of the effort signal.)

Still another example of an "amplitude feature" (now in a flow signal like FIG. 9) is a region in such a signal in which relatively large amplitude excursions indicate that the patient is breathing effectively. One such period of effective breathing is indicated by the reference tb in FIG. 11. Such a period is to be compared with other periods of much lower amplitude excursion in the flow signal. Such low amplitude excursion periods are periods in which the patient is not breathing effectively.

With regard to references to time, "relative time" may be the time of an event or amplitude feature in a signal (e.g., the effort signal) relative to the time of another event or amplitude feature in that same signal (e.g., the effort signal) or in another signal (e.g., the flow signal). "Elapsed time" refers to the time between the occurrence of two events, either in the same signal or in two different signals.

Figure 15B:
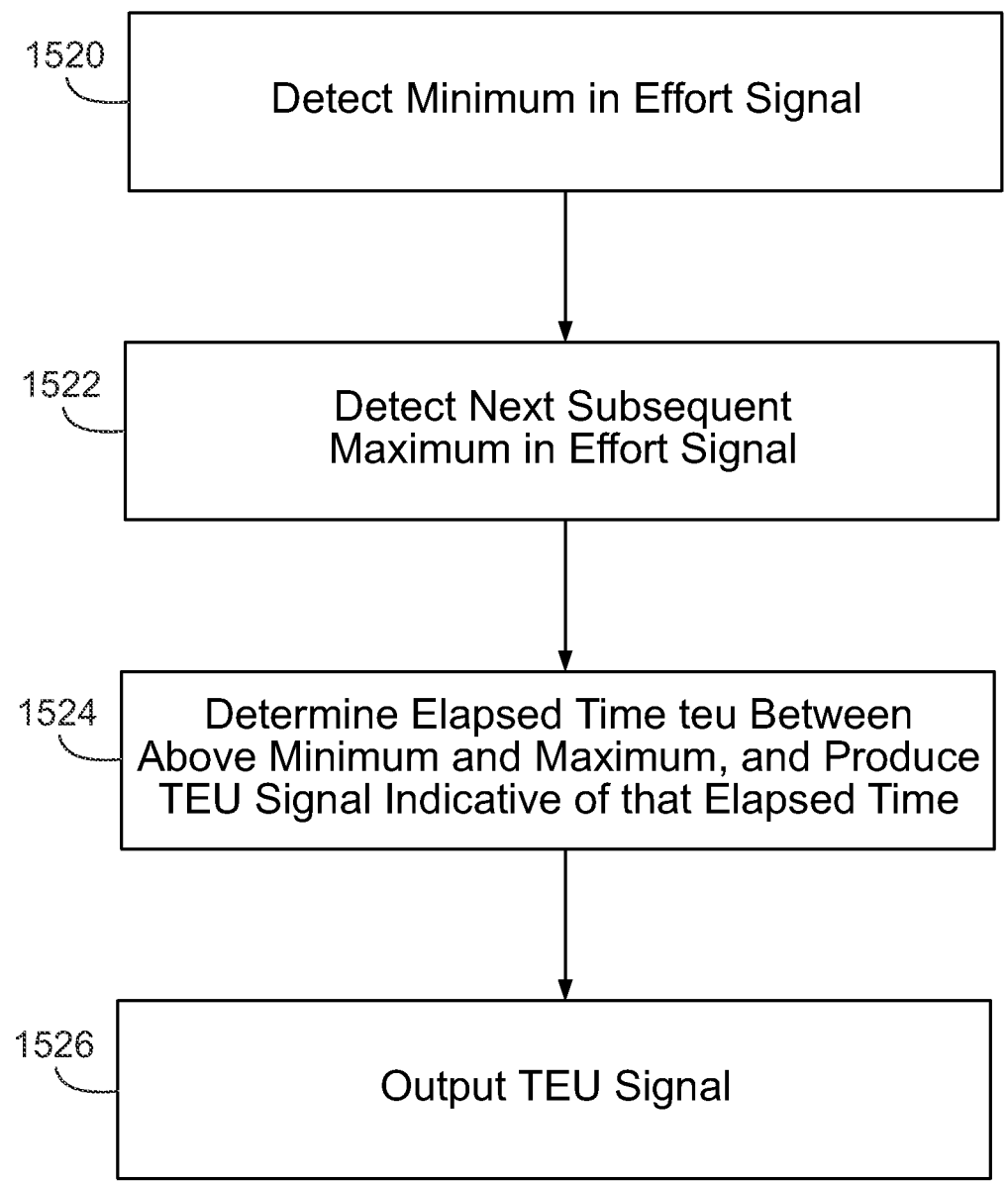

Returning to the "general matter" referred to at the start of an earlier paragraph, an example of "extracting from the effort signal a respiratory characteristic signal for the patient that is based on at least one amplitude feature of the effort signal and a relative time of occurrence of that amplitude feature" is developing the TEU signal as in FIG. 14a. FIG. 15b similarly shows illustrative method steps for developing the TEU signal, and it will be apparent from the following description of FIG. 15b that in this specific TEU example the "at least one amplitude feature" is either a minimum or a maximum in the amplitude of the effort signal, and "the relative time of occurrence of that amplitude feature" is the elapsed time between such a minimum and maximum. The TEU signal is only one example of what is covered by the general statement quoted above, and other examples will be recognized as being detailed elsewhere in this disclosure.

Turning now to FIG. 15b, in step 1520 a minimum (e.g., 1112b in FIG. 11) in the amplitude of the effort signal is detected. In step 1522, a next subsequent maximum (e.g., 1110b in FIG. 11) in the amplitude of the effort signal is detected. In step 1524, the elapsed time (e.g., teu in FIG. 11) between the above minimum and maximum is determined in order to produce a TEU signal indicative of that elapsed time. (Note that circuitry 1436 in FIG. 14a is an example of circuitry that can perform steps like 1520-1524.) In step 1526, the TEU signal is output (e.g., as at 1444 in FIG. 14b).

Figure 15C:
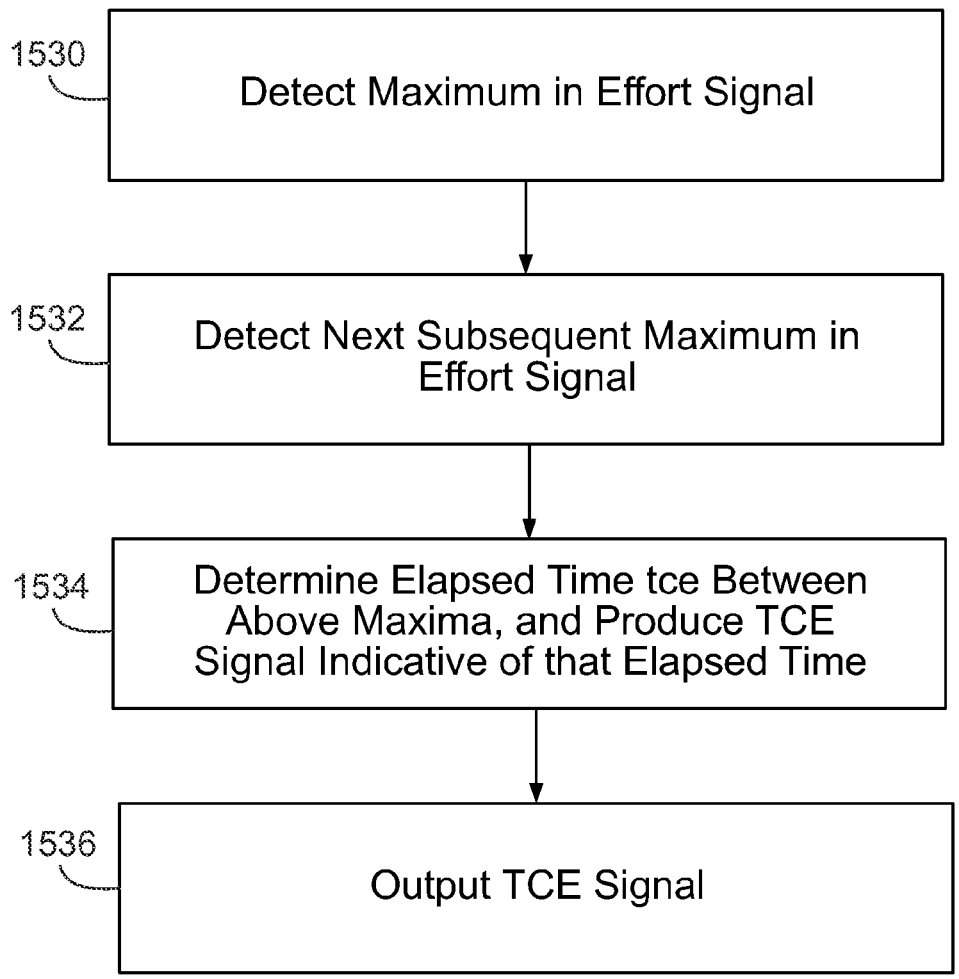

FIG. 15c shows illustrative method steps that can be used to provide a TCE signal, similar to what is described earlier in connection with element 1440 in FIG. 14b. In step 1530, a maximum (e.g., 1110b in FIG. 11) in the amplitude of the effort signal is detected. In step 1532, a next subsequent maximum (e.g., 1110c in FIG. 11) in the amplitude of the effort signal is detected. In step 1534, the elapsed time (teu in FIG. 11) between the above two maxima is determined in order to enable production of a TCE signal indicative of that elapsed time. In step 1536, the TCE signal is output (e.g., as at 1444 in FIG. 14b).

Figure 15D:
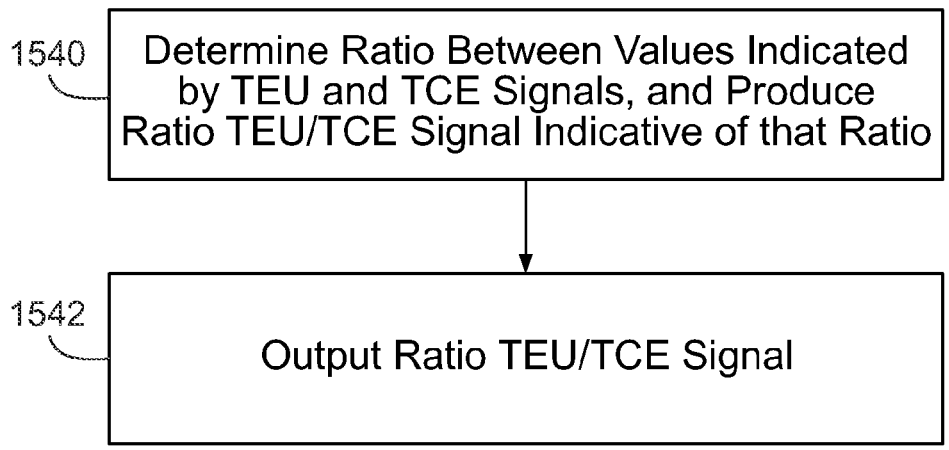

FIG. 15d shows illustrative method steps that can be used to provide a ratio TEU/TCE signal, similar to what is described earlier in connection with element 1442 in FIG. 14b. In step 1540, a ratio between the values indicated by the TEU signal (e.g., from step 1524) and the TCE signal (e.g., from step 1534) is determined. Also in step 1540, this ratio is used to produce the ratio TEU/TCE signal. In step 1542, the ratio TEU/TCE signal is output (e.g., as at 1444 in FIG. 14b).

Figure 15E:
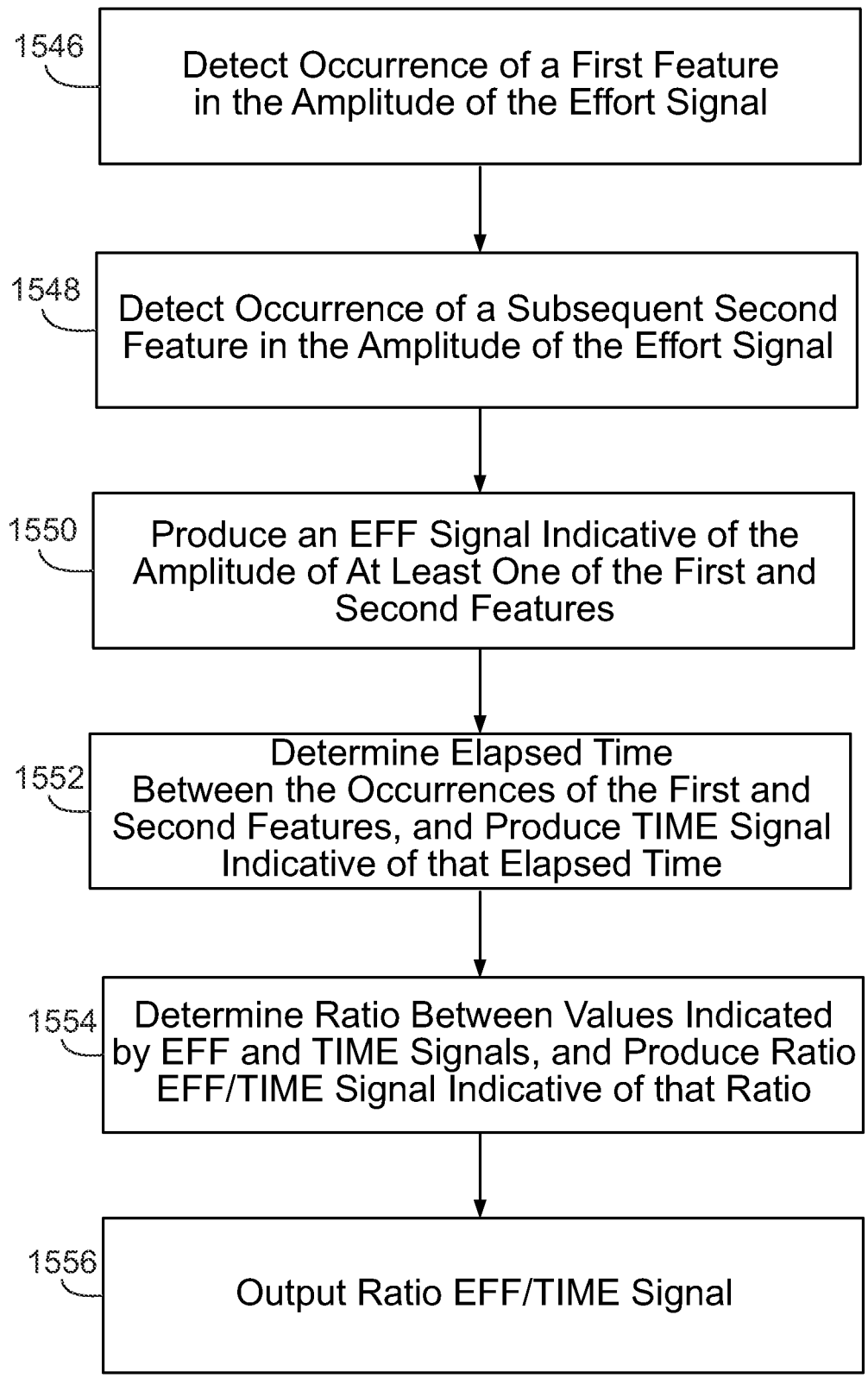

FIG. 15e shows illustrative method steps that can be used to provide a ratio EFF/TIME signal, similar to what is described above in connection with elements 1450-1454 in FIG. 14c. In step 1546, occurrence of a first feature (e.g., a minimum) in the amplitude of the effort signal is detected. In step 1548, occurrence of a second feature (e.g., a maximum) in the amplitude of the effort signal is detected. In step 1550, an EFF signal indicative of the amplitude of the effort signal at one of the above features (e.g., the maximum) is produced. At step 1552, the elapsed time between the above features is determined in order to produce a TIME signal. In step 1554 a ratio between the values indicated by the EFF and TIME signals is determined in order to produce a ratio EFF/TIME signal indicative of that ratio. In step 1556, the ratio EFF/TIME signal is output (e.g., as at 1444 in FIG. 14b).

Figure 15F:
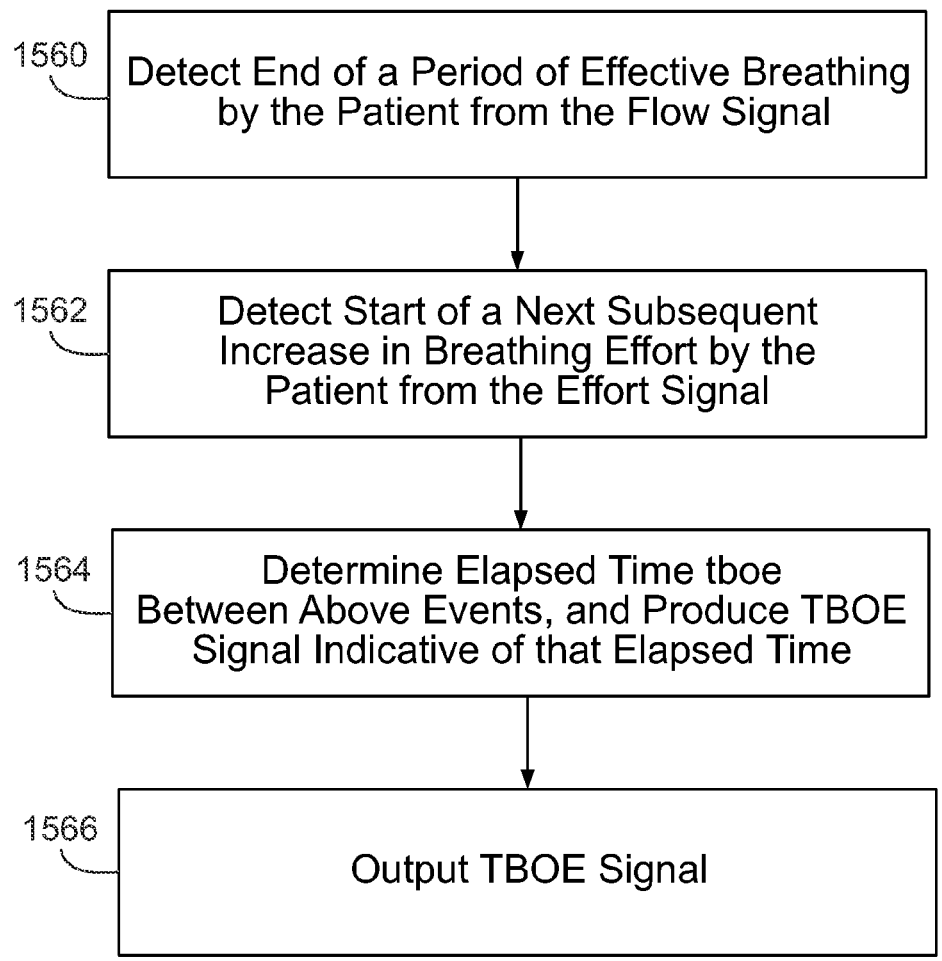

FIG. 15f shows illustrative method steps that can be used to produce a TBOE signal, similar to what is described above in connection with elements 1460-1464 in FIG. 14d. This is an example of an embodiment that employs a flow meter, and therefore steps 1512 and 1516 in FIG. 15a. This is also an example of producing a respiratory characteristic signal based on amplitude and the time features of both an effort signal and a flow signal. In step 1560, the end of a period of effective breathing by the patient (e.g., the end of period tb in FIG. 11) is detected from the flow signal. In step 1562 the start of a next subsequent increase in breathing effort by the patient (e.g., at 1112b in FIG. 11) is detected from the effort signal. In step 1564, the elapsed time (tboe in FIG. 11) between the above two events is determined in order to produce a TBOE signal indicative of that elapsed time. In step 1566, the TBOE signal is output (e.g., as at 1444 in FIG. 14b).

Figure 15G:
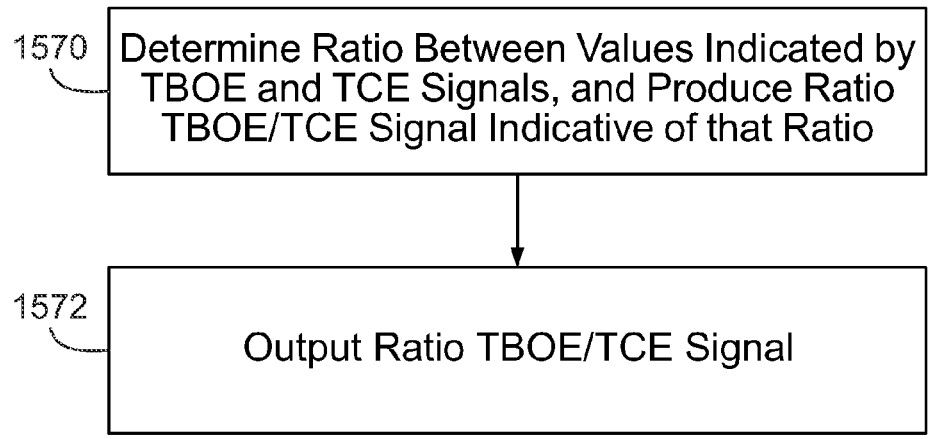

FIG. 15g shows illustrative method steps that can be used to provide a ratio TBOE/TCE signal, similar to what is described earlier in connection with element 1470 in FIG. 14e. In step 1570, a ratio between the values indicated by the TBOE signal (e.g., from step 1564) and the TCE signal (e.g., from step 1534) is determined. Also in step 1570, this ratio is used to produce the ratio TBOE/TCE signal. In step 1572, the ratio TBOE/TCE signal is output (e.g., as at 1444 in FIG. 14b).

Figure 15H:
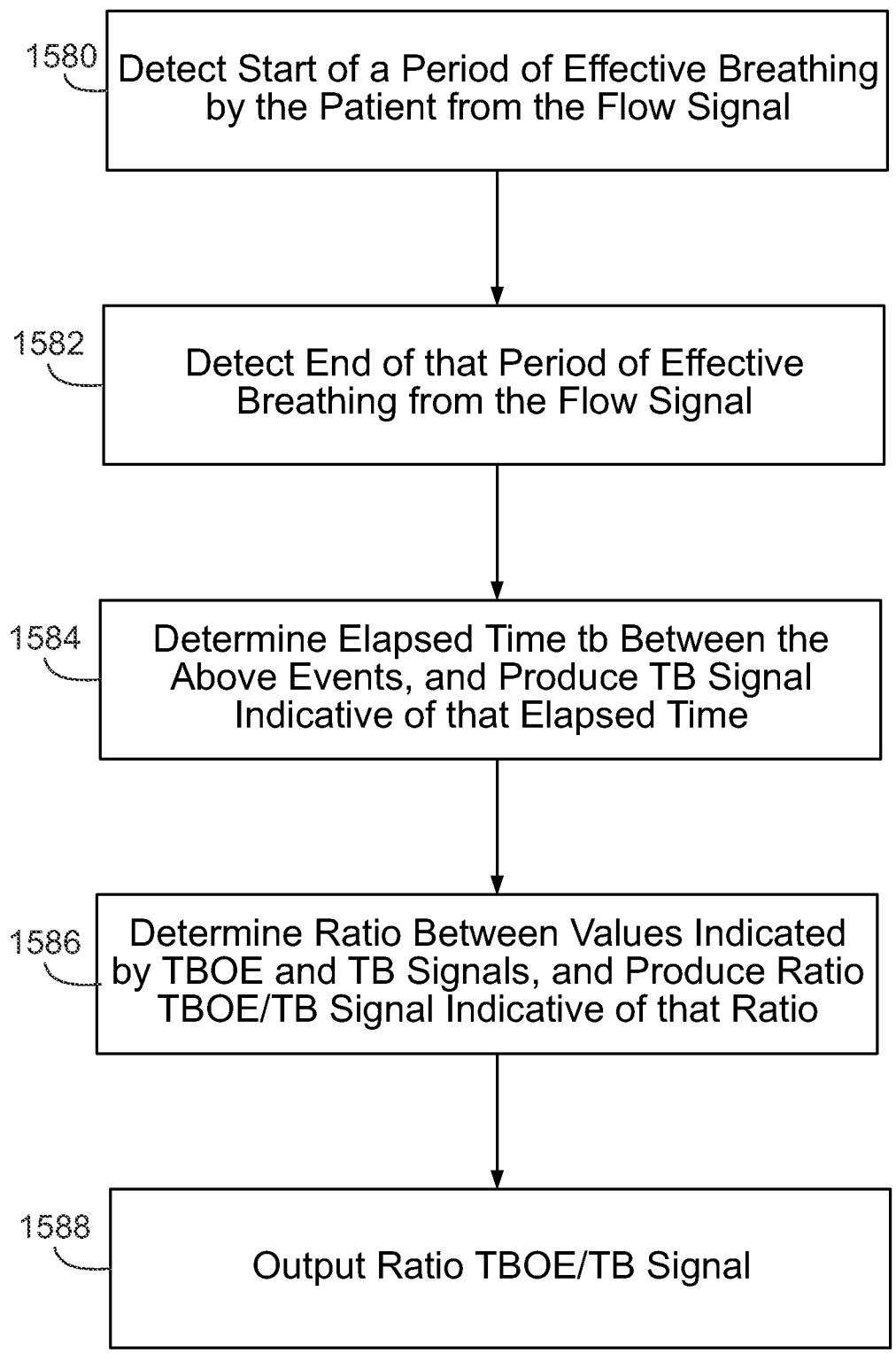

FIG. 15h shows illustrative method steps that can be used to provide a ratio TBOE/TB signal, similar to what is described earlier in connection with elements 1472 and 1474 in FIG. 14e. This is another example of an embodiment that employs a flow meter, and therefore steps 1512 and 1516 in FIG. 15*a*. This is also another example of producing a respiratory characteristic signal based on amplitude and time features of both an effort signal and a flow signal. In step 1580, the start of a period of effective breathing by the patient (e.g., the start of period tb in FIG. 11) is detected from the flow signal. In step 1582, the end of that period is detected. In step 1584, the elapsed time (tb in FIG. 11) between the above two events is determined in order to produce a TB signal indicative of that elapsed time. In step 1586, a ratio between the values indicated by the TBOE signal (e.g., from step 1564) and the TB signal is determined in order to produce the ratio TBOE/TB signal indicative of that ratio. In step 1588, the ratio TBOE/TB signal is output (e.g., as at 1444 in FIG. 14*b*).

Figure 15I:
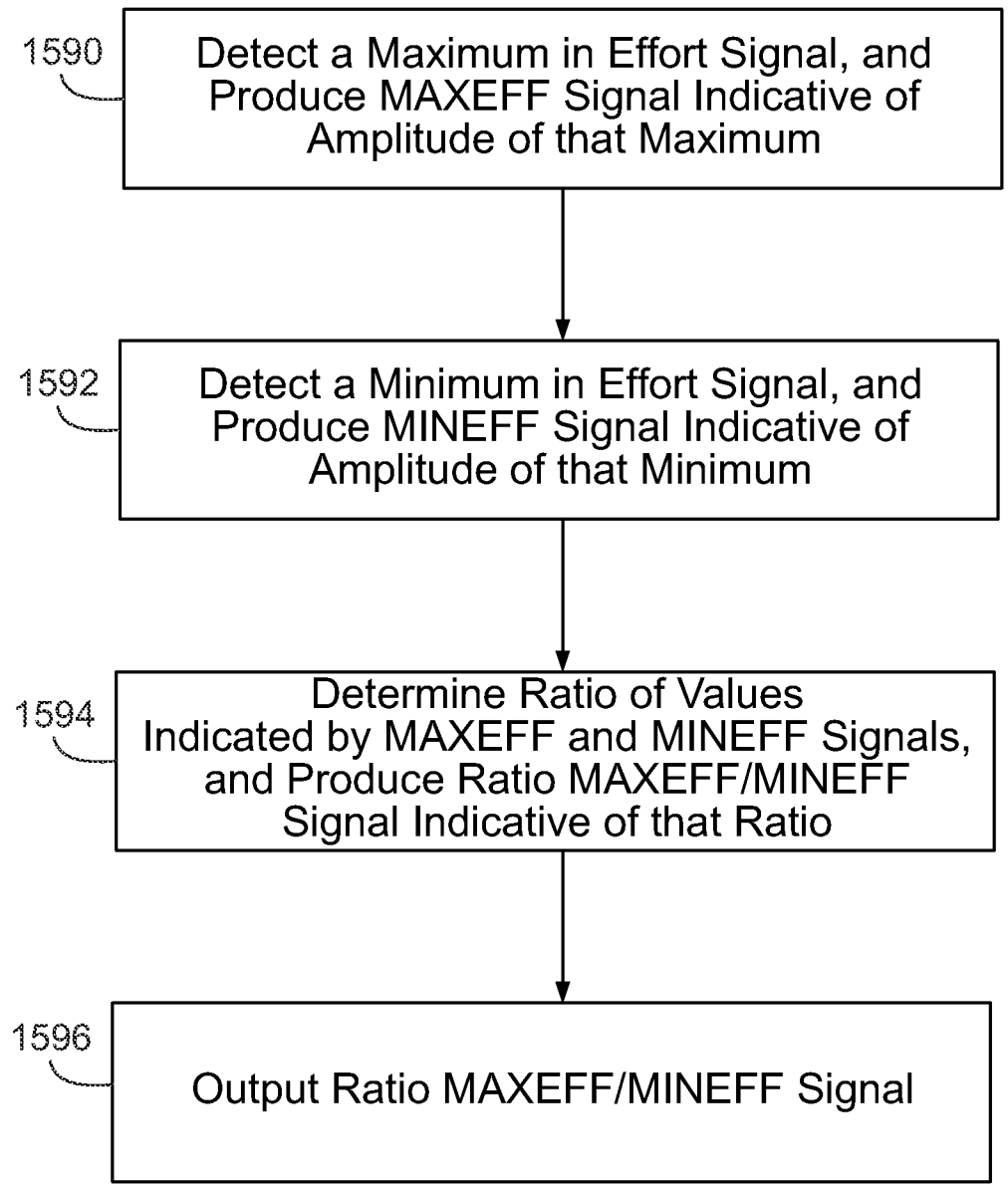

FIG. 15*i* shows illustrative method steps that can be used to provide a ratio MAXEFF/MINEFF signal, similar to what is described earlier in connection with elements 1480-1484 in FIG. 14*f*. This is an example of using amplitude features of a signal or signals without a need to also consider time, relative time, or elapsed time. In step 1590, a maximum (e.g., at 1110*a* in FIG. 11) in the amplitude of the effort signal is detected in order to produce a MAXEFF signal. In step 1592, a minimum (e.g., at 1112*b* in FIG. 11) in the amplitude of the effort signal is detected in order to produce a MINEFF signal. For example, this minimum may be the next subsequent minimum following the maximum detected in step 1590. In step 1594, a ratio between the values indicated by the MAXEFF and MINEFF signals is determined in order to produce the ratio MAXEFF/MINEFF signal indicative of that ratio. In step 1596, the ratio MAXEFF/MINEFF signal is output (e.g., as at 1444 in FIG. 14*b*).

It will be understood that the foregoing is only illustrative of the principles of this disclosure, and that various modifications can be made by those skilled in the art without departing from the scope and spirit of the disclosure. For example, the order in which certain steps are performed can be different from the order illustrated and described herein. Similarly, instead of certain of the ratios illustrated and described herein, reciprocals of those ratios may be more useful and/or informative and may therefore be formed as alternatives or additions. In some cases, apparatus elements that are shown as separate herein can be combined into a smaller number of multi-function apparatus elements. The respiratory characteristics shown and described herein are only examples, and other characteristics can be produced instead or in addition following the general principles of this disclosure.

The following claims may also describe various aspects of this disclosure.

What is claimed is:

1. Apparatus for determining a respiratory characteristic of a patient comprising:
    apparatus for coupling to the patient to produce a patient monitor signal containing signal information indicative of effort the patient is exerting to breathe;
    first circuitry for extracting from the patient monitor signal a breathing effort signal indicative of the patient's exertion of effort in order to breathe; and
    second circuitry for:
        detecting first and second amplitude features of the effort signal;
        determining, using the effort signal, an elapsed time between the first amplitude feature of the effort signal and the second amplitude feature of the effort signal; and
        extracting a respiratory characteristic signal for the patient that is based on the elapsed time.

2. The apparatus defined in claim 1 wherein the elapsed time is from a minimum to a subsequent maximum in the amplitude of the effort signal.

3. The apparatus defined in claim 1 wherein elapsed time is from one maximum to a next subsequent maximum in the amplitude of the effort signal.

4. The apparatus defined in claim 1 a first precursor respiratory characteristic signal is indicative of the elapsed time, wherein the second circuitry is further adapted to extract from the effort signal a second precursor respiratory characteristic signal for the patient that is based on at least one other amplitude feature of the effort signal, and wherein the second circuitry is still further adapted to produce a further respiratory characteristic signal for the patient that is indicative of a ratio between the first and second precursor respiratory characteristic signals.

5. The apparatus defined in claim 4 wherein elapsed time is from a minimum to a subsequent maximum in the amplitude of the effort signal, and wherein the second precursor signal is indicative of an elapsed time from one maximum to a next subsequent maximum in the amplitude of the effort signal.

6. The apparatus defined in claim 4 wherein the second precursor signal is indicative of a magnitude of an amplitude feature of the effort signal.

7. The apparatus defined in claim 1 further comprising:
    a flow meter for coupling to the patient to produce a breathing air flow signal for the patient, wherein the flow signal is applied to the second circuitry, and wherein the respiratory characteristic signal is additionally based on at least one amplitude feature of the flow signal and a relative time of occurrence of that flow signal amplitude feature.

8. The apparatus defined in claim 7 wherein the amplitude feature of the flow signal indicates cessation of effective breathing by the patient, and wherein an amplitude feature of the effort signal indicates commencement of an increase in breathing effort by the patient.

9. The apparatus defined in claim 8 wherein the respiratory characteristic signal is additionally based on an elapsed time between the amplitude feature of the flow signal and the amplitude feature of the effort signal indicating commencement of an increase in breathing effort by the patient.

10. The apparatus defined in claim 7 wherein the respiratory characteristic signal comprises a first precursor respiratory characteristic signal, wherein the second circuitry is further adapted to extract a second precursor respiratory characteristic signal, at least in part, from the flow signal, and wherein the second circuitry is still further adapted to produce a further respiratory characteristic signal for the patient that is indicative of a ratio between the first and second precursor respiratory characteristic signals.

11. The apparatus defined in claim 10 wherein the first precursor signal is indicative of the elapsed time and wherein the elapsed time is between two successive maximum amplitude features in the effort signal.

12. The apparatus defined in claim 11 wherein the second precursor signal is indicative of an elapsed time between (1) cessation of effective breathing by the patient as indicated by the flow signal, and (2) commencement of an increase in breathing effort by the patient as indicated by the effort signal.

13. The apparatus defined in claim 12 wherein the second precursor signal indicates duration of a period of effective breathing by the patient as indicated by the flow signal.

14. The apparatus defined in claim 1 wherein the first circuitry comprises:
    scalogram circuitry for producing scalogram signals indicative of the patient monitor signal; and breathing effort extraction circuitry for extracting the effort signal from the scalogram signals.

15. The apparatus defined in claim 1 wherein the apparatus for coupling to the patient comprises:
photoplethysmograph ("PPG") apparatus for coupling to the patient to produce a PPG signal as the patient monitor signal.

16. Apparatus for determining a respiratory characteristic of a patient comprising:
apparatus for coupling to the patient to produce a patient monitor signal containing signal information indicative of effort the patient is exerting to breathe;
first circuitry for extracting from the patient monitor signal a breathing effort signal indicative of the patient's exertion of effort in order to breathe; and
second circuitry for:
  detecting two amplitude features of the effort signal;
  determining a ratio of the two amplitude features;
  extracting from the effort signal a respiratory characteristic signal for the patient based on the ratio.

17. The apparatus of claim 1 wherein extracting from the effort signal the respiratory characteristic signal comprises:
determining the elapsed time between a first maximum or minimum in the effort signal and a second maximum or minimum in the effort signal, wherein the first maximum or minimum in the effort signal corresponds to the first amplitude feature.

\* \* \* \* \*